(12) United States Patent
Krämer et al.

(10) Patent No.: US 6,414,000 B1
(45) Date of Patent: Jul. 2, 2002

(54) SUBSTITUTED DIPHENYL OXAZOLIN DERIVATIVES WITH INSECTICIDAL EFFECT

(75) Inventors: Wolfgang Krämer, Burscheid; Udo Kraatz, Leverkusen; Reinhard Lantzsch, Wuppertal; Albrecht Marhold, Leverkusen; Christoph Erdelen, Leichlingen; Ulrike Wachendorff-Neumann, Neuwied; Andreas Turberg, Haan; Norbert Mencke, Leverkusen, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/402,966

(22) PCT Filed: Apr. 14, 1998

(86) PCT No.: PCT/EP98/02182

§ 371 (c)(1),
(2), (4) Date: Oct. 12, 1999

(87) PCT Pub. No.: WO98/47881

PCT Pub. Date: Oct. 29, 1998

(30) Foreign Application Priority Data

Apr. 24, 1997 (DE) .......................................... 197 17 228

(51) Int. Cl.⁷ ........................ C07D 263/14; A01N 43/76
(52) U.S. Cl. ...................................... 514/374; 548/237
(58) Field of Search ........................... 548/237; 514/374

(56) References Cited

U.S. PATENT DOCUMENTS 5,141,948 A * 8/1992 Miyamoto .................. 514/365

OTHER PUBLICATIONS

Houben Weyl, vol. VI/Ic, (month unavailable) 1976 pp. 216 and 251,Methoden der Organischen Chemie (p. 216) K.F. Wedemeyer: Ein– und mehrwertige Phenole, (p. 251) Substitution der Amino–Gruppe durch die Hydroxy–Gruppe.

* cited by examiner

*Primary Examiner*—Robert Gerstl
(74) *Attorney, Agent, or Firm*—Joseph C. Gil; Jackie Ann Zurcher

(57) ABSTRACT

The present invention relates to novel oxazoline derivatives of the formula (I)

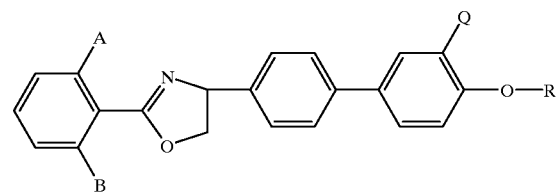

in which the radicals A, B, Q and R are each as defined in the description to processes for their preparation and to their use for controlling animal pests.

33 Claims, No Drawings

SUBSTITUTED DIPHENYL OXAZOLIN DERIVATIVES WITH INSECTICIDAL EFFECT

TECHNICAL FIELD OF THE INVENTION

The present invention relates to novel substituted oxazoline derivatives, to processes for their preparation and to their use for controlling animal pests.

BACKGROUND OF THE INVENTION

It is already known that oxazoline derivatives have insecticidal and acaracidal activity (cf. for example EP-A 0 432 661, EP-A 0 696 584, WO-A 95/04726, WO-A 96/11190 or WO-A 96/22283), for example. 2-(2,6-difluorophenyl)-4-(4'-methoxy- or isopropoxy biphenyl-4-yl)-1,3-oxazoline (cf. EP-A 0 432 661).

However, the efficacy and/or the duration of action of these known compounds, in particular against certain organisms or at low application concentrations, is not entirely satisfactory in all areas of use.

DETAILED DESCRIPTION OF THE INVENTION

This invention, accordingly, provides novel substituted oxazoline derivatives of the formula (I)

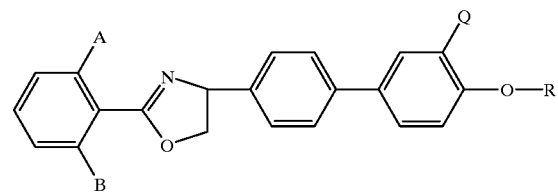

(I)

in which the radicals A, B, Q and R are each as defined in Table 1 below:

TABLE 1

| Comp. No. | A | B | Q | R |
|---|---|---|---|---|
| 1 | F | F | H | —CH$_2$—C$_6$H$_4$—CF$_3$ |
| 2 | Cl | H | H | —CH$_2$—C$_6$H$_4$—CF$_3$ |
| 3 | F | Cl | H | —CH$_2$—C(CH$_3$)=N—O—CH(CH$_3$)C$_2$H$_5$ |
| 4 | F | Cl | H | —C(CH$_3$)$_2$—C(CH$_3$)=N—O—C$_3$H$_7$-i |
| 5 | Br | H | H | —C$_3$H$_7$-i |
| 6 | F | F | H | —CO—NH—C$_3$H$_7$-i |
| 7 | F | F | H | —CF=CF—CH=CH$_2$ |
| 8 | F | F | H | —CH$_2$—CH=NOCH$_3$ |
| 9 | H | Cl | H | —C$_3$H$_7$-n |
| 10 | H | Cl | H | —CH$_2$—C$_6$H$_4$—C$_4$H$_9$-t |
| 11 | H | Cl | H | —C$_3$H$_7$-i |
| 12 | H | Cl | H | —C$_4$H$_9$-n |
| 13 | H | Cl | H | —CH$_2$—C$_6$H$_{11}$ |
| 14 | H | Cl | H | —CH$_2$—C$_3$H$_7$-i |
| 15 | F | F | H | —CH$_2$CH$_2$—CH=CF$_2$ |
| 16 | F | F | H | —CH$_2$—CH=NOC$_2$H$_5$ |
| 17 | F | F | H | —CH$_2$—C$_6$H$_4$—F |
| 18 | F | F | H | —CH$_2$—(2,4-di-CH$_3$-C$_6$H$_3$) |

TABLE 1-continued

| Comp. No. | A | B | Q | R |
|---|---|---|---|---|
| 19 | F | F | H | −CH₂−C₆H₄−CN (4-cyanobenzyl) |
| 20 | F | F | H | −CH₂−(2,3-dichlorophenyl) |
| 21 | F | F | H | −CH₂−C₆H₄−OCF₃ (4-OCF₃-benzyl) |
| 22 | I | H | H | −CH₂−(2,2-dichlorocyclopropyl) |
| 23 | F | F | H | −CH₂−C₆H₄−SCF₃ (4-SCF₃-benzyl) |
| 24 | F | F | H | −CH₂−(2-fluorophenyl) |
| 25 | F | F | H | −CH₂−(3-fluorophenyl) |
| 26 | F | F | H | −CH₂−(3-COOCH₃-phenyl) |
| 27 | F | Cl | H | −C₃H₇-i |
| 28 | F | F | H | cyclopentyl (H) |
| 29 | F | Cl | H | −C₃H₇-n |
| 30 | F | Cl | H | −CH₂−C₃H₇-i |
| 31 | F | F | H | −CH₂−C₆H₄−SO₂CH₃ (4-SO₂CH₃-benzyl) |
| 32 | F | F | H | −CH₂−(2-CF₃-phenyl) |

TABLE 1-continued

| Comp. No. | A | B | Q | R |
|---|---|---|---|---|
| 33 | F | F | H | —CH$_2$—C$_6$H$_4$(3-CF$_3$) |
| 34 | F | Cl | H | —C$_4$H$_9$-n |
| 35 | F | F | H | —CH(CH$_3$)—CH=NOCH$_3$ |
| 36 | F | F | H | —CH(CH$_3$)—C≡CH |
| 37 | Cl | H | H | —CH(CH$_3$)—C≡CH |
| 38 | Cl | F | H | —CO—C$_6$H$_3$(2-F, 6-Cl) |
| 39 | Cl | H | H | —CH$_2$—C$_3$H$_7$-i |
| 40 | Cl | Cl | H | —CH$_2$—C$_6$H$_4$(4-CF$_3$) |
| 41 | Cl | Cl | H | —C$_3$H$_7$-i |
| 42 | F | F | H | —CH$_2$—C(C(CH$_3$)$_2$—C=CCl$_2$)=N—OC$_2$H$_5$ |
| 43 | F | F | Cl | —CH(CH$_3$)—C(CH$_3$)=N—OC$_3$H$_7$ |
| 44 | F | F | Cl | —CH(CH$_3$)—C(CH$_3$)=NOH |
| 45 | Cl | H | Cl | —CH(CH$_3$)—C(CH$_3$)=NOH |
| 46 | F | F | H | —C(CH$_3$)$_2$—C(CH$_3$)=N—OC$_3$H$_7$-i |
| 47 | F | Cl | H | —CH(CH$_3$)—C(CH$_3$)=N—OCH$_2$—C$_3$H$_7$-i |
| 48 | F | Cl | H | —CH(CH$_3$)—C(CH$_3$)=N—O—CH(CH$_3$)C$_2$H$_5$ |
| 49 | F | Cl | H | —CH(CH$_3$)—C(CH$_3$)=N—O—C$_4$H$_9$-n |
| 50 | F | F | H | —CH(CH$_3$)—C(CH$_3$)=N—O—CH(CH$_3$)C$_2$H$_5$ |

TABLE 1-continued

| Comp. No. | A | B | Q | R |
|---|---|---|---|---|
| 51 | F | F | H | —CH(CH$_3$)—C(CH$_3$)=N—O—CH$_2$—C$_3$H$_7$-i |
| 52 | F | F | H | —CH(CH$_3$)—C(CH$_3$)=N—OC$_4$H$_9$-n |
| 53 | F | F | H | —C(CH$_3$)$_2$—CH=NOC$_2$H$_5$ |
| 54 | F | Cl | H | —CH$_2$—C(CH$_3$)=N—OCH$_2$—C$_3$H$_7$-i |
| 55 | F | F | H | —CH$_2$—C(CH$_3$)=N—OC$_4$H$_9$-n |
| 56 | F | F | H | —CH$_2$—C(CH$_3$)=N—O—CH(CH$_3$)C$_2$H$_5$ |
| 57 | F | F | H | —C(CH$_3$)$_2$—CH=NOCH$_3$ |
| 58 | Cl | H | H | —C(CH$_3$)$_2$—C(CH$_3$)=N—OC$_3$H$_7$-i |
| 59 | F | F | H | —C(CH$_3$)$_2$—C(CH$_3$)=N—O—CH(CH$_3$)C$_2$H$_5$ |
| 60 | F | F | H | —C(CH$_3$)$_2$—C(CH$_3$)=N—O—C$_4$H$_9$-n |
| 61 | Cl | H | Cl | —CH(CH$_3$)—C(CH$_3$)=N—O—C$_4$H$_9$-n |
| 62 | Cl | H | Cl | —CH(CH$_3$)—C(CH$_3$)=N—O—CH(CH$_3$)C$_2$H$_5$ |
| 63 | F | F | Cl | —CH(CH$_3$)—C(CH$_3$)=N—O—C$_4$H$_9$-n |
| 64 | F | F | Cl | —CH(CH$_3$)—C(CH$_3$)=N—O—CH(CH$_3$)C$_2$H$_5$ |
| 65 | Cl | Cl | H | —CH(CH$_3$)—COCH$_3$ |
| 66 | Cl | Cl | H | —CH(CH$_3$)—C(CH$_3$)=N—OCH$_3$ |
| 67 | Cl | Cl | H | —CH(CH$_3$)—C(CH$_3$)=N—OC$_2$H$_5$ |
| 68 | Br | H | H | —CH(CH$_3$)—COCH$_3$ |
| 69 | Cl | H | H | CF$_3$ |
| 70 | CH$_3$O— | H | H | CF$_3$ |
| 71 | CF$_3$ | H | H | CF$_3$ |
| 72 | CH$_3$SO$_2$— | H | H | CF$_3$ |

TABLE 1-continued

| Comp. No. | A | B | Q | R |
|---|---|---|---|---|
| 73 | $C_2H_5O-$ | H | H | $CF_3$ |
| 74 | $i-C_3H_7O-$ | H | H | $CF_3$ |
| 75 | $NO_2$ | H | H | $CF_3$ |
| 76 | $CH_3O-$ | F | H | $CF_3$ |
| 77 | F | $NH_2$ | H | $CF_3$ |
| 78 | $CH_3S-$ | H | H | $CF_3$ |
| 79 | $i-C_3H_7S-$ | H | H | $CF_3$ |
| 80 | $C_2H_5S-$ | H | H | $CF_3$ |
| 81 | $C_2H_5O-$ | F | H | $CF_3$ |
| 82 | $C_2H_5CH(CH_3)O-$ | F | H | $CF_3$ |
| 83 | $C_2H_5CH(CH_3)O-$ | $C_2H_5CH(CH_3)O-$ | H | $CF_3$ |
| 84 | $i-C_3H_7CH_2O-$ | F | H | $CF_3$ |
| 85 | $i-C_3H_7CH_2O-$ | $i-C_3H_7CH_2O-$ | H | $CF_3$ |
| 86 | $C_2H_5$ | H | H | $CF_3$ |
| 87 |  | H | H | $CF_3$ |
| 88 | $CH_3O$ | H | H | $C_3H_7-i$ |
| 89 | Br | H | H | $CF_3$ |
| 90 | I | H | H | $CF_3$ |
| 91 | Br | H | H | $-CH(CH_3)-CH(OH)CH_3$ |
| 92 | Br | H | H | $-CH(CH_3)-C(CH_3)=NOCH_3$ |
| 93 | I | H | H | $C_3H_7-i$ |
| 94 | I | H | H | 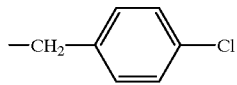 |
| 95 | Br | H | H | $-CH_2-CH=CH_2$ |
| 96 | Br | H | H | $-CH_2-C\equiv CH$ |
| 97 | F | H | Cl | 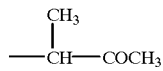 |
| 98 | F | H | Cl | 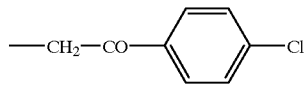 |
| 99 | F | Cl | H | 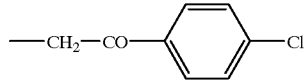 |
| 100 | F | H | H | $-CH(CH_3)-COCH_3$ |
| 101 | F | H | H | 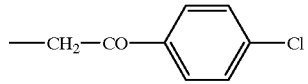 |
| 102 | F | F | H | $-C(CH_3)_2-CHO$ |
| 103 | F | H | Cl | 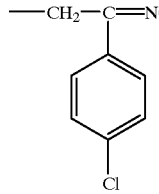 |

TABLE 1-continued

| Comp. No. | A | B | Q | R |
|---|---|---|---|---|
| 104 | F | Cl | H | 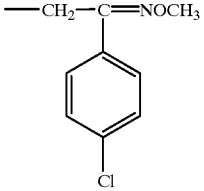 |
| 105 | F | H | Cl | 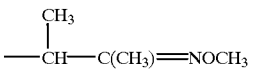 |
| 106 | F | H | Cl | 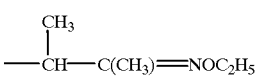 |
| 107 | F | H | H | —C$_3$H$_7$-i |
| 108 | F | H | H | —CH$_2$—C$_3$H$_7$-i |
| 109 | F | H | H | 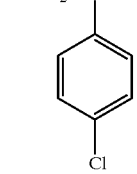 |
| 110 | F | H | H |  |
| 111 | F | H | H |  |
| 112 | F | Cl | H | —CH$_2$—CH=NOCH$_3$ |
| 113 | F | Cl | H | —CH$_2$—CH=NOC$_2$H$_5$ |
| 114 | F | F | Cl | —CH$_2$—CH=NOCH$_3$ |
| 115 | F | F | Cl | —CH$_2$—CH=NOC$_2$H$_5$ |
| 116 | Cl | H | Cl | —CH$_2$—CH=NOCH$_3$ |
| 117 | Cl | H | Cl | —CH$_2$—CH=NOC$_2$H$_5$ |
| 118 | F | H | Cl | —CH$_2$CF$_3$ |
| 119 | F | F | CH$_3$ | —CH$_2$CF$_3$ |
| 120 | CF$_3$CH$_2$O— | F | CH$_3$ | —CH$_2$CF$_3$ |
| 121 | Cl | H | —CH$_2$—CH=CH$_2$ | —CH$_2$CF$_3$ |
| 122 | Cl | H | CH$_3$ | —CH$_2$CF$_3$ |
| 123 | F | F | C$_2$H$_5$ | CH$_2$CF$_3$ |
| 124 | Cl | H | H | —CH$_2$CF$_3$ |
| 125 | F | F | H | 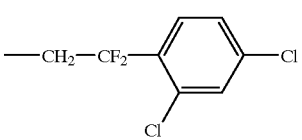 |
| 126 | F | F | H | —CH$_2$—CF$_2$—CHF$_2$ |
| 127 | F | F | H | —(CH$_2$)$_3$—CF$_2$—CF$_3$ |

The substituted oxazoline derivatives of the formula (I) can be present as optical and/or geometrical isomers, which depends, among other things, on the substituents. The present invention provides both the isomer mixtures and the pure isomers.

Furthermore, it was found that the substituted oxazoline derivatives of the formula (I)/(Table 1) are obtained when hydroxybiphenyloxazolines of the formula (II)

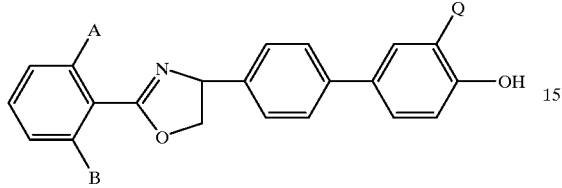

(II)

in which
  A, B and Q are each as defined above in Table 1 are reacted with a compound of the formula (III)

M—R   (III)

in which
  R is in each case as defined above in Table 1 and
  M is a leaving group,
  if appropriate in the presence of a base and/or catalyst and if appropriate in the presence of a diluent.

Furthermore, it was found that the novel substituted oxazoline derivatives of the formula (I) are highly suitable for controlling animal pests, in particular insects, arachnids, and nematodes, encountered in agriculture, in forestry, in the protection of stored products and of materials, and in the hygiene sector.

The formula (I)/Table 1 provides a general definition of the compounds according to the invention. Preferred compounds are listed in Table 1 a below:

TABLE IA (I)

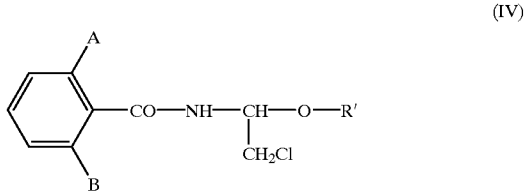

| Cpd.No. | A | B | Q | R |
|---|---|---|---|---|
| 1A | F | F | H | —CH$_2$—C$_6$H$_4$—CF$_3$ |
| 2A | Cl | H | H | —CH$_2$—C$_6$H$_4$—CF$_3$ |
| 3A | F | Cl | H | —CH$_2$—C(CH$_3$)=N—O—CH(CH$_3$)C$_2$H$_5$ |
| 4A | F | Cl | H | —C(CH$_3$)$_2$—C(CH$_3$)=N—O—C$_3$H$_7$-i |
| 5A | Br | H | H | —C$_3$H$_7$-i |

Using, for example, 2-(2,6-difluorophenyl)-4-(4'-hydroxybiphenyl-4-yl)1,3-oxazoline and 4-trifluoromethylbenzyl chloride as starting materials for carrying out the process according to the invention, the course of the reaction can be represented by the following equation:

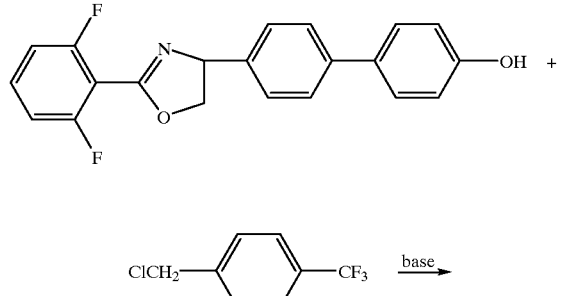

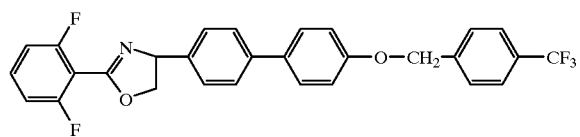

Starting compounds of formula (II) are known (cf. for example EP-A 432 661 and EP-A 696 584) and/or can be obtained, as described therein, in a generally well-known manner by converting an amide-derivative of the formula (IV)

(IV)

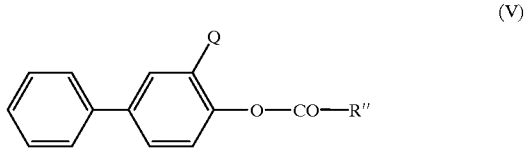

in which
  A and B are each as defined above in Table 1 and
  R' represents C$_1$–C$_4$-alkyl, preferably methyl or ethyl,
with biphenyl derivatives of the formula (V)

(V)

in which
  Q is as defined above in Table 1 and
  R'' represents C$_1$–C$_4$-alkyl or C$_1$–C$_4$-alkoxy, preferably methyl, ethyl, methoxy or ethoxy,
  in the presence of an acid catalyst such as, for example, hydrofluoric acid, sulphuric acid, acetic acid or aluminium chloride and in the presence of a diluent such as, for example, methylene chloride or acetonitrile, at temperatures between 0° C. and 80° C.;

cyclizing the resulting compounds of the formula (VI)

(VI)

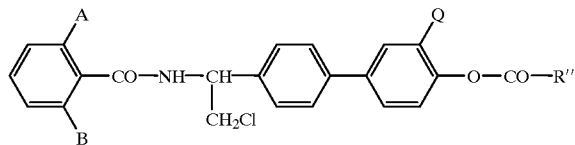

in which

A, B, Q and R" are each as defined above in the presence of a base such as, for example, aqueous sodium hydroxide solution, if appropriate in the presence of a catalyst such as, for example, ammonium compounds and if appropriate in the presence of a diluent such as, for example, dimethylformamide, at temperatures between 0° C. and 100° C. to give biphenyloxazolines of the formula (VII)

(VII)

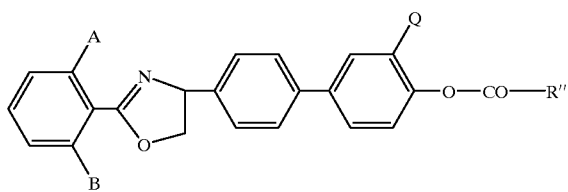

in which

A, B, Q and R" are each as defined above, and hydrolysing these in a customary manner in the presence of the diluent such as, for example, methanol at room temperature, using, for example, aqueous ammonia, it being possible, if appropriate, to carry out cyclization and hydrolysis in a one-part reaction.

Not known and likewise part of the subject matter of this application is the compound (II-1) of the formula (II).

(II-1)

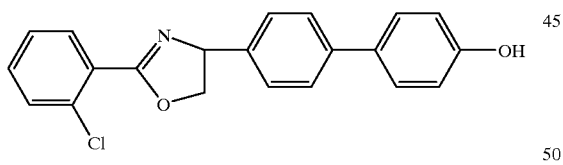

The amide derivatives of the formula (IV) are known (cf. for example EP-A 594 179) and/or can be obtained by methods described therein.

The formula (III) provides a general definition of the compounds also to be used as starting materials in the process according to the invention. In the formula (III), M represents a customary leaving group, preferably halogen, in particular chlorine or bromine; alkylsulphonyloxy, in particular methylsulphonyloxy; or optionally substituted arylsulphonyloxy, in particular phenylsulphonyloxy, p-chlorophenylsulphonyloxy or tolylsulphonyloxy.

The compounds of the formula (III) are generally known compounds of organic chemistry.

Suitable diluents for carrying out the process according to the invention are all customary solvents. Preference is given to using optionally halogenated aromatic or aliphatic hydrocarbons, ketones, nitrites and amides. Examples include toluene, acetone, acetonitrile, dimethylformamide and dimethylacetamide.

Suitable bases for carrying out the process according to the invention are all customary inorganic and organic bases. Examples include tertiary amines such as triethylamine, DBN (diazabicyclononene), DBU (diazabicycloundecene), DABCO (diazabicyclooctane), alkali metal and alkaline earth metal hydroxides such as, for example, sodium hydroxide, potassium hydroxide and calcium hydroxide, and alkali metal and alkaline earth metal carbonates such as, for example, sodium carbonate and potassium carbonate.

If appropriate, the process according to the invention is carried out in the presence of a phase-transfer catalyst. Examples include quaternary ammonium salts, such as tetraoctylammonium bromide or benzyltriethylammonium chloride and tris(3,6-dioxaheptyl)amine (TDA).

When carrying out the process according to the invention, the reaction temperatures may be varied within a relatively wide range. In general, the reaction is carried out at temperatures between −20° C. and 100° C., preferably between 0° C. and 60° C.

When carrying out the process according to the invention, approximately equimolar amounts are generally employed. However, it is also possible to use an excess of the compound of the formula (III).

Work-up and isolation is carried out in the customary manner.

The compounds of the formula (I) according to the invention can also be obtained by A) reacting, in a first step, compounds of the formula (VIII)

(VIII)

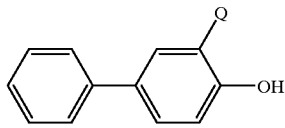

in which

Q is as defined above with a compound of the formula (III)

M—R (III)

in which

M and R are each as defined above, under the conditions of the process according to the invention;

B) reacting, in a second step, the resulting compounds of the formula (IX)

(IX)

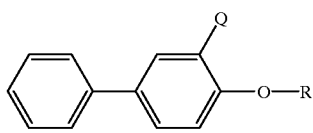

in which

Q and R are each as defined above, with acetyl chloride in the presence of a diluent such as, for example, methylene chloride or dichloroethane and in the presence of an acid suitable for Friedel-Crafts reactions or a Lewis acid such as, for example, tetrafluoroboric acid or aluminium chloride, at temperatures between −20° C. and +50° C.;

C) chlorinating or brominating, in a third step, the resulting compounds of the formula (X)

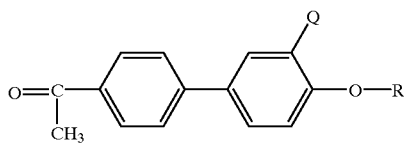

(X)

in which

Q and R are each as defined above, if appropriate in the presence of a diluent such as, for example, methylene chloride or carbon tetrachloride, at temperatures between −10° C. and 25° C.;

D) reacting, in a fourth step, the resulting compounds of the formula (XI)

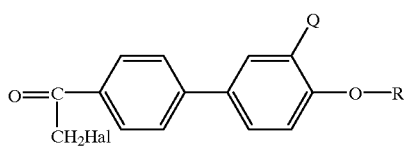

(XI)

in which

Q and R are each as defined above and

Hal represents chlorine or bromine with a formic acid salt such as, for example, sodium formate, in the presence of a diluent, if appropriate in a mixture with water, such as, for example, ethanol/water, and, if appropriate, in the presence of a phase-transfer catalyst such as, for example, quaternary ammonium salts, at temperatures between 50° C. and 150° C.;

E) reacting, in a fifth step, the resulting, compounds of the formula (XII)

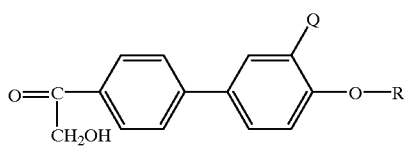

(XII)

in which

Q and R are each as defined above, with O-methylhydroxylamine, if appropriate in the form of a salt, for example the hydrochloride, in the presence of a diluent, for example alcohols or ethers, and, if appropriate, in the presence of a base, for example sodium acetate, at temperatures between 0° C. and 60° C.;

F) reacting, in a sixth step, the resulting compounds of the formula (XIII)

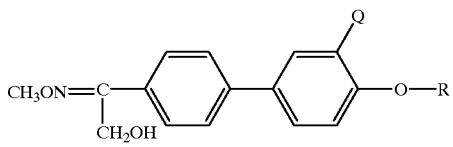

(XIII)

in which

Q and R are each as defined above, with a reducing agent such as, for example, sodium borohydride, in the presence of an acid such as, for example, trifluoroacetic acid and, if appropriate, in the presence of a diluent such as, for example, tetrahydrofuran at temperatures between 0° C. and 120° C.;

G) reacting, in a seventh step, the resulting compounds of the formula (XIV)

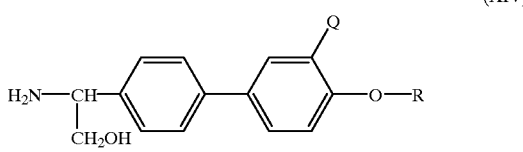

(XIV)

in which

Q and R are each as defined above with benzoyl chlorides of the formula (XV)

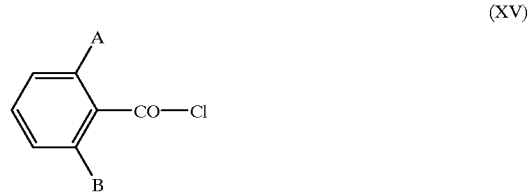

(XV)

in which

A and B are each as defined above, if appropriate in the presence of a base such as, for example, triethylamine and, if appropriate, in the presence of a diluent such as, for example, tetrahydrofuran, at temperatures between 0° C. and 100° C.;

H) reacting, in an eighth step, the resulting compounds of the formula (XVI)

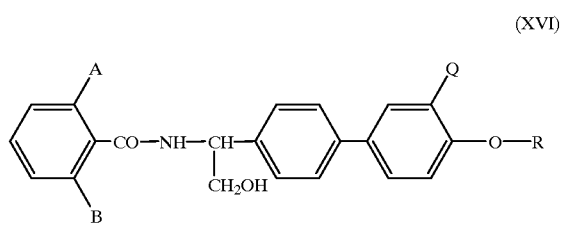

(XVI)

in which

A, B, Q and R are each as defined above with a chlorinating agent such as, for example, thionyl chloride, if appropriate in the presence of a diluent such as, for example, toluene, at temperatures between 20° C. and 100° C.;

I) cyclizing, in a ninth step, the resulting compounds of the formula (XVII)

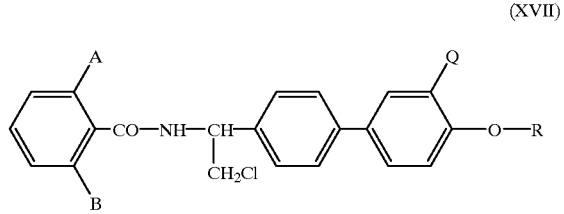

(XVII)

in which

A, B, Q and R are each as defined above in the presence of a base such as, for example, aqueous sodium hydroxide solution; if appropriate in the presence of a phase-transfer catalyst such as, for example, ammonium compounds and, if appropriate, in the presence of a diluent such as, for example, dimethylformamide at temperatures between 0° C. and 100° C., to give the compounds of the formula (I) according to the invention.

The compounds of the formula (XVII) can also be obtained directly by reacting amide derivatives of the formula (IV) with compounds of the formula (IX) in the presence of an acid catalyst such as, for example, hydrogen fluoride, boron trifluoride, titanium chloride or aluminium chloride, and in the presence of a diluent such as, for example, methylene chloride or acetonitrile, at temperatures between 0° C. and 80° C.

The starting materials of the formula (VIII) are known and/or can be prepared in a simple manner by known methods.

The compounds of the formula (VIII) are obtained, for example, by sulphonating optionally substituted biphenyls, followed by reaction with alkali metal hydroxides, to give the hydroxybiphenyls, or by diazotization and boiling of aminobiphenyls (cf. for example Houben-Weyl, Volume VI/Ic (1976), pages 216 and 251).

Benzoyl chlorides of the formula (XV) are generally known compounds of organic chemistry.

The active compounds have good crop safety and favourable mammalian toxicity and are suitable for controlling animal pests, in particular insects, arachnids and nematodes, which are encountered in agriculture, in forestry, in the protection of stored products and of materials, and in the hygiene field. They are preferably employed as crop protection agents and are active against normally sensitive and resistant species and against all or some stages of development. The abovementioned pests include:

From the order of Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and Scutigera spec.

From the order of the Symphyla, for example, *Scutigerella immaculata.*

From the order of the Thysanura, for example, *Lepisma sacchiarina.*

From the order of the Collembola, for example, *Onychiurus armatus.*

From the order of the Orthoptera, for example, *Blatta orientalis, Periplaneta americana, Leucophaea maderae, Blatella germanica, Acheta domesticus,* Gryllotalpa spp., Locusta migratoria migratorioides, Melanoplus differentialis and Schistocerca gregaria.

From the order of the Dermaptera, for example, *Forficula auricularia.*

From the order of the Isoptera, for example, Reticulitermes spp.

From the order of the Anoplura, for example, *Pediculus humanus corporis,* Haematopinus spp. and Linognathus spp.

From the order of the Mallophaga, for example, Trichodectes spp. and Damalinea spp.

From the order of the Thysanoptera, for example, *Hercinothrips femoralis* and *Thrips tabaci.*

From the order of the Heteroptera, for example, Euryaster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum, Aphis gossypii, Brevicoryne brassicae, Cryptomiyzus ribis, Aphis fabae, Aphis pomi, Eriosoma lanigerum, Hyalopterus arundinis, Phylloxera vastatrix,* Pemphigus spp., *Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp, *Bucculatrix thurberiella, Phyllocnistis citrella,* Agrotis spp., Euxoa spp., Feltia spp., *Earias insulana,* Heliothis spp., *Spodoptera exigua, Mamestra brassicae, Panolis flammea, Spodoptera litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.*

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhiynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica.*

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.*

From the order of the Siphonaptera, for example, *Xenopsylla cheeopis* and Ceratophyllus spp.

From the order of the Arachnida, for example, *Scorpio maurus* and *Latrodectus mactans*

From the order of the Acarina, for example, *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp.

The phytoparasitic nematodes include, for example, Pratylenchus spp., *Radopholus similis, Ditylenchus dipsaci,*

*Tylenchulus semipenetrans*, Heterodera spp., Globodera spp., Meloidogyne spp., Aphelenchoides spp., Longidorus spp., Xiphinema spp., Trichodorus spp.

The compounds of the formula (I) according to the invention in particular have high insecticidal and acaricidal activity.

They can be used to particularly good effect for controlling insects which are injurious to plants, such as, for example, against the caterpillars of the cotton bollworm (*Heliothis armigera*), the larvae of the mustard beetle (*Phaedon cochleariae*), the caterpillars of the diamond back moth (*Plutella xylostella*), the caterpillars of the owlet moth (*Spodoptera frugiperda* or *exigua*), or for controlling mites which are injurious to plants, such as, for example, against the fruit tree red spider mite (*Panonychus ulmi*) or the greenhouse red spider mite (*Tetranychus urticae*).

The active compounds can be converted into the customary fomulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

If the extender used is water, it is also possible to use for example organic solvents as auxiliary solvents suitable liquid solvents are essentially: aromatics, such as xylene, toluene or alkylnaphthalenes, chlorinated aromatics and chlorinated aliphatic hydrocarbons, Such as chlorobenzenes, chloroethylenes or methylene chloride, aliphatic hydrocarbons, such as cyclohexane or paraffins, for example petroleum fractions, mineral and vegetable oils, alcohols, such as butanol or glycol and their ethers and esters, ketones, such as acetone, methyl ethyl ketone, methyl isobutyl ketone or cyclohexanone, strongly polar solvents, such as dimethylformamide and dimethyl sulphoxide, and water.

Suitable solid carriers are:
for example ammonium salts and ground natural minerals, such as kaolins, clays, talc, chalk, quartz, attapulgite, montmorillonite or diatomaceous earth, and ground synthetic minerals, such as finely divided silica, alumina and silicates, suitable solid carriers for granules are: for example crushed and fractionated natural rocks such as calcite, marble, pumice, sepiolite and dolomite and synthetic granules of inorganic and organic meals, and granules of organic material such as sawdust, coconut shells, maize cobs and tobacco stalks; suitable emulsifiers and foam-formers are: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolysates; suitable dispersing agents are: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, and natural phospholipids such as cephalins and lecithins, and synthetic phospholipids, can be used in the formulations. Possible further additives are mineral and vegetable oils.

It is possible to use colourants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compound according to the invention can be present in its commercially available formulations and in the use forms prepared from these formulations, as a mixture with other active compounds, such as insecticides, attractants, sterilizing agents, bactericides, acaricides, nematicides, fungicides, growth-regulating substances or herbicides. The insecticides include, for example, phosphates, carbamates, carboxylates, chlorinated hydrocarbons, phenylureas and substances produced by microorganisms.

Examples of particularly advantageous mixture components are the following compounds:

Fungicides:
2-aminobutane; 2-anilino-4-methyl-6-cyclopropyl-pyrimidine; 2',6'-dibromo-2-methyl-4'-trifluoromethoxy-4'-trifluoro-methyl- 1,3-thiazole-5-carboxanilide, 2,6-dichloro-N-(4-trifluoromethylbenzyl)-benzamide; (E)-2-methoxyimino-N-methyl-2-(2-phenoxyphlenyl)-acetamide; 8-hydroxyquinoline sulphate; methyl (E)-2-{2-[6-(2-cyanophenoxy)-pyrimidin-4-yloxy]-phenyl}-3-methoxyacrylate; methyl (E)-methoximino-[alpha-(o-tolyloxy)-o-tolyl]-acetate; 2-phenylphenol (OPP), aldimorph, ampropylfos, anilazine, azaconazole, benalaxyl, benodanil, benomyl, binapacryl, biphenyl, bitertanol, blasticidin-S, bromuconazole, bupirimate, buthiobate, calcium polysulphide, captafol, captan, carbendazim, carboxin, quinomethionate, chiloroneb, chloropicrin, chlorothalonil, chlozolinate, cufraneb, cymoxanil, cyproconazole, cyprofuram, dichlorophen, diclobutrazol, diclofluanid, diclomezin, dicloran, diethiofencarb, difenoconazole, dimethirimol, dimethomorph, diniconazole, dinocap, diphenylaminie, dipyrithion, ditalimfos, dithianon, dodine, drazoxolon, edifenphos, epoxyconazole, ethirimol, etridiazole, fenarimol, fenbuconazole, fenfuram, fenitropan, fenpiclonil, fenpropidin, fenpropimorph, fentin acetate, fentin hydroxide, ferbam, ferimzone, fluazinam, fludioxonil, fluoromide, fluquinconazole, flusilazole, flusulphamide, flutolanil, flutriafol, folpet, fosetyl-aluminium, fthalide, fuberidazole, furalaxyl, furmecyclox, guazatine, hexachlorobenzene, hexaconazole, hymexazol, imazalil, imibenconazole, iminoctadine, iprobenfos (IBP), iprodione, isoprothiolane, kasugamycin, copper preparations such as: copper hydroxide, copper naphthenate, copper oxychloride, copper sulphate, copper oxide, oxine-copper and Bordeaux mixture, mancopper, mancozeb, maneb, mepanipyrim, mepronil, metalaxyl, metconazole, methasulphocarb, methfuroxam, metiram, metsulphovax, myclobutanil, nickel dimethyldithiocarbamate, nitrothal-isopropyl, nuarimol, ofurace, oxadixyl, oxamocarb, oxycarboxin, pefurazoate, penconazole, pencycuron, phosdiphen, phthalide, pimaricin, piperalin, polycarbamate, polyoxin, probenazole, prochloraz, procymidone, propamocarb, propiconazole, propineb, pyrazophos, pyrifenox, pyrimethanil, pyroquilon, quintozene (PCNB), sulphur and sulphur preparations, tebuconazole, tecloftalam, tecnazene, tetraconazole, thiabendazole, thicyofen, thiophanatemethyl, thiram, tolclophos-methyl, tolylfluanid, triadimefon, triadimenol, triazoxide, trichlamide, tricyclazole, tridemorph, triflumizole, triforine, triticonazole, validamycin A, vinclozolin, zineb, ziram.

Bactericides:

bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/Acaricides/Nematicides:

abamectin, AC 303 630, acephate, acrinathrin, alanycarb, aldicarb, alphamethrin, amitraz, avermectin, AZ 60541, azadirachtin, azinphos A, azinphos M, azocyclotin, Bacillus thuringiensis, bendiocarb, benfuracarb, bensultap, beta-cyfluthrin, bifenthrin, BPMC, brofenprox, bromophos A, bufencarb, buprofezin, butocarboxim, butylpyridaben, cadusafos, carbaryl, carbofuran, carbophenothion, carbosulphan, cartap, CGA 157 419, CGA 184699, chloethocarb, chlorethoxyfos, chlorfenvinphos, chlorfluazuron, chlormephos, chlorpyrifos, chlorpyrifos M, cis-resmethrin, clocythrin, clofentezine, cyanophos, cycloprothrin, cyfluthrin, cyhalothrin, cyhexatin, cypermethrin, cyromazine, deltamethrin, demeton-M, demeton-S, demneton-S-methyl, diafenthiuron, diazinon, dichlofenthion, dichlorvos, dicliphos, dicrotophos, diethion, diflubenzuron, dimethoate, dimethylvinphos, dioxathion, disulphoton, edifenphos, emamectin, esfenvalerate, ethiofencarb, ethion, ethiofenprox, ethoprophos, etrimphos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, flucycloxuron, flucythrinate, flufenoxuron, flufenprox, fluvalinate, fonophos, formothion, fosthiazate, fubfenprox, furathiocarb, HCH, heptenophos, hexaflumuron, hexythiazox, imidacloprid, iprobenfos, isazophos, isofenphos, isoprocarb, isoxathion, ivermectin, lambda-cyhalothrin, lufenuron, malathion, mecarbam, mevinphos, mesulphenphos, metaldehyde, methlacrifos, methamidophos, methidathion, methiocarb, methomyl, metolcarb, milbemectin, monocrotophos, moxidectin, naled, NC 184, NI 25, nitenpyram, omethoate, oxamyl, oxydemethon M, oxydeprofos, parathion A, parathion M, permethrin, phenthoate, phorate, phosalone, phosmet, phosphamidon, phoxim, pirimicarb, pirimiphos M, pirimiphos A, profenofos, promecarb, propaphos, propoxur, prothiofos, prothoate, pymetrozin, pyrachlophos, pyridaphenthion, pyresmethrin, pyrethrum, pyridaben, pyrimidifen, pyriproxifen, quinalphos,

RH 5992, salithion, sebufos, silafluofen, sulphotep, suliprofos, tebufenozid, tebufenpyrad, tebupirimiphos, teflubenzuron, tefluthrin, temephos, terbam, terbufos, tetrachlorvinphos, thiafenox, thiodicarb, thiofanox, thiomethon, thionazin, thuringiensin, tralomethrin, triarathen, triazophos, triazuron, trichlorfon, triflumuron, trimethacarb, vamidothion, XMC, xylylcarb, YI 5301/5302, zetamethrin A mixture with other known active compounds such as herbicides, or with fertilizers and growth-regulators is also possible.

The active compounds according to the invention can furthermore be present in its commercially available formulations and in the use forms prepared from these formulations, as a mixture with synergistic agents. Synergistic agents are compounds which increase the action of the active compounds without it being necessary for the synergistic agent added to be active itself.

The active compound content of the use forms prepared from in the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compounds have excellent residual action on wood and clay and good stability to alkali on limed substrates. The active compounds according to the invention are not only active against plant, hygiene and stored-product pests, but also, in the veterinary medicine sector, against animal parasites (ectoparasites), such as ixodid ticks, argasid ticks, scab mites, trombiculid mites, flies (stinging and sucking), parasitic fly larvae, lice, hair lice, bird lice and fleas. These parasites include:

From the order of the Anoplurida, for example, Haematopinus spp., Linognathus spp., Pediculus spp., Phtirus spp. and Solenopotes spp.

From the order of the Mallophagida and the sub-orders Amblycerina and Ischnocerina, for example, Trimenopon spp., Menopon spp., Trinoton spp., Bovicola spp., Werneckiella spp., Lepikentron spp., Damalina spp., Trichodectes spp. and Felicola spp.

From the order Diptera and the sub-orders Nematocerina and Brachycerina, for example, Aedes spp., Anopheles spp., Culex spp., Simulium spp., Eusimulium spp., Phlebotomus spp., Lutzomyia spp., Culicoides spp., Chrysops spp., Hybomitra spp., Atylotus spp., Tabanus spp., Haematopota spp., Philipomyia spp., Braula spp., Musca spp., Hydrotaea spp., Stomoxys spp., Haematobia spp., Morellia spp., Fannia spp., Glossina spp., Calliphora spp., Lucilia spp., Chrysomyia spp., Wohlfahrtia spp., Sarcophaga spp., Oestrus spp., Hypoderma spp., Gasterophilus spp., Hippobosca spp., Lipoptena spp. and Melophagus spp.

From the order of the Siphonapterida, for example, Pulex spp., Ctenocephalides spp., Xenopsylla spp. and Ceratophyllus spp.

From the order of the Heteropterida, for example, Cinmex spp., Triatoma spp., Rhodnius spp. and Panstrongylus spp.

From the order of the Blattarida, for example, *Blatta orientalis, Periplaneta americana, Blattela germanica* and *Supella* spp.

From the sub-class of the Acaria (Acarida) and the orders of the Meta- and Mesostigmata, for example Argas spp., Ornithodorus spp., Otabius spp., Ixodes spp., Amblyomma spp., Boophilus spp., Dermacentor spp., Haemaphysalis spp., Hyalomma spp., Rhipicephalus spp., Dermanyssus spp., Raillietia spp., Pneumonyssus spp., Stemostoma spp. and Varroa spp.

From the order of the Actinedida (Prostigmata) and Acaridida (Astigmata), for example Acarapis spp., Cheyletiella spp., Ornithocheyletia spp., Myobia spp., Psorergates spp., Demodex spp., Trombicula spp., Listrophorus spp., Acarus spp., Tyrophagus spp., Caloglyphus spp., Hypodectes spp., Pterolichius spp., Psoroptes spp., Chorioptes spp., Octodectes spp., Sarcoptes spp., Notoedres spp., Knemidocoptes spp., Cytodites spp. and Laminosioptes spp.

The active compounds of the formula (I) according to the invention are also suitable for controlling arthropods which attack agricultural livestock, such as, for example, cattle, sheep, goats, horses, pigs, donkeys, camels, buffalo, rabbits, chickens, turkeys, ducks, geese, honey bees, other domestic animals, such as, for example, dogs, cats, cage birds, aquarium fish, and so-called experimental animals such as, for example, hamsters, guinea-pigs, rats and mice. By controlling these arthropods, it is intended to reduce mortality and decreased performance (in meat, milk, wool, hides, eggs, honey and the like), so that more economical and simpler animal keeping is made possible by using the active compounds according to the invention.

In the veterinary sector, the active compounds according to the invention are used in a known manner by enteral administration, for example in the form of tablets, capsules, drinks, drenches, granules, pastes, boluscs, the feed-through method, suppositories, by parenteral administration, such as, for example, by means of injections (intramuscular, subcutaneous, intravenous, intraperitoneal and the like), implants, by nasal application, by dermal administration, for example in the form of dipping or bathing, spraying, pouring-on and spotting-on, washing, dusting, and with the aid of shaped articles which comprise active compound, such as collars, ear tags, tail marks, limb bands, halters, marking devices and the like.

When administered to livestock, poultry, domestic animals and the like, the active compounds of the formula (I) can be used as formulations (for example powders, emulsions, flowables) which comprise the active compounds in an amount of 1 to 80% by weight, either directly or after dilution by a factor of 100 to 10,000, or they may be used in the form of a chemical bath.

Furthermore, it has been found that the compounds of the formula (I) according to the invention have a potent insecticidal action against insects which destroy industrial materials.

The following, insects may be mentioned by way of example and as being preferred, but without any limitation:

Beetles, such as

Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis, Xyleborus spec., Tryptodendron spec. Apate monachus, Bostrychus capucins, Heterobostrychus brunneus, Sinoxylon spec. Dinoderus minutus.

Dermapterans, such as

Sirex juvencus, Urocerus gigas, Urocerus gigas taignus, Urocerus augur.

Termites, such as

Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus.

Bristletails, such as

Lepisma saccharina.

Industrial materials are to be understood as meaning, in the present context, non-live materials such as, preferably, synthetic materials, glues, sizes, paper and board, leather, wood and timber products, and paint.

The materials to be very particularly protected against attack by insects are wood and timber products.

Wood and timber products which can be protected by the composition according to the invention or mixtures comprising such a composition are to be understood as meaning, for example, construction timber, wooden beams, railway sleepers, bridg,e components, jetties, wooden vehicles, boxes, pallets, containers, telephone poles, wood lagging, windows and doors made of wood, plywood, particle board, joiner's articles, or wood products which, quite generally, are used in the construction of houses or in joinery.

The active compounds can be used as such, in the form of concentrates or generally customary formulations, such as powders, granules, solutions, suspensions, emulsions or pastes.

The formulations mentioned can be prepared in a manner known per se, for example by mixing the active compounds with at least one solvent or diluent, emulsifier, dispersant and/or binder or fixative, water repellent, if appropriate desiccants and UV stabilizers and, if appropriate, colourants and pigments and other processing auxiliaries.

The insecticidal compositions or concentrates used for the protection of wood and wooden materials comprise the active compound according to the invention at a concentration of 0.0001 to 95% by weight, in particular 0.001 to 60% by weight.

The amount of the compositions or concentrates employed depends on the species and the occurrence of the insects and on the medium. The optimum rate of application can be determined upon use in each case by test series. However, in general, it suffices to employ 0.0001 to 20% by weight, preferably 0.001 to 10% by weight, of the active compound, based on the material to be protected.

The solvent and/or diluent used is an organochemical solvent or solvent mixture and/or an oily or oil-type organochemical solvent or solvent mixture of low volatility and/or a polar organochemical solvent or solvent mixture and/or water and, if appropriate, an emulsifier and/or wetting agent.

Organochemical solvents which are preferably employed are oily or oil-type solvents having an evaporation number of above 35 and a flashpoint of above 30° C., preferably above 45° C. Substances which are used as such oily and oil-type solvents which have low volatility and are insoluble in water are suitable mineral oils or their aromatic fractions, or mineral-oil-containing solvent mixtures, preferably white spirit, petroleum and/or alkylbenzene.

Substances which are advantageously used are mineral oils with a boiling range of 170 to 220° C., white spirit with a boiling range of 170 to 220° C., spindle oil with a boiling range of 250 to 350° C., petroleum or aromatics of boiling range 160 to 280° C., essence of turpentine and the like.

In a preferred embodiment, liquid aliphatic hydrocarbons with a boiling range of 180 to 210° C. or high-boiling mixtures of aromatic and aliphatic hydrocarbons with a boiling range of 180 to 220° C. and/or spindle oil and/or monochloronaphthalene, preferably a-monochloronaphthalene, are used.

The organic oily or oil-type solvents of low volatility having an evaporation number of above 35 and a flashpoint of above 30° C., preferably above 45° C., can be partially replaced by organochemical solvents of high or medium volatility, with the proviso that the solvent mixture also has an evaporation number of above 35 and a flashpoint of above 30° C., preferably above 45° C., and that the insecticide/fungicide mixture is soluble or emulsifiable in this solvent mixture.

In a preferred embodiment, part of the organochemical solvent or solvent mixture is replaced by an aliphatic polar organochemical solvent or solvent mixture. Substances which are preferably used are aliphatic organochemical solvents having hydroxyl and/or ester and/or ether groups, such as, for example, glycol ether, esters and the like.

The organochemical binders used within the scope of the present invention are the synthetic resins and/or binding drying oils which are known per se and can be diluted with water and/or are soluble or dispersible or emulsifiable in the organochemical solvents employed, in particular binders composed of, or comprising, an acylate resin, a vinyl resin, for example polyvinyl acetate, polyester resin, polycondensation or polyaddition resin, polyurethane resin, alkyd resin or modified alkyd resin, phenol resin, hydrocarbon resin, such as indene/coumarone resin, silicone resin, drying vegetable and/or drying oils and/or physically drying binders based on a natural and/or synthetic resin.

The synthetic resin used as the binder can be employed in the form of an emulsion, dispersion or solution. Up to 10% by weight of bitumen or bituminous substances can also be used as binders. In addition, colourants, pigments, water repellents, odour-masking substances and inhibitors or anticorrosives known per se and the like can also be employed.

The composition or the concentrate preferably comprises, in accordance with the invention, at least one alkyd resin or modified alkyd resin and/or a drying vegetable oil as the organochemical binder. Preferably used according to the invention are alkyd resins with an oil content of over 45% by weight, preferably 50 to 68% by weight.

All or some of the abovementioned binder can be replaced by a fixative (mixture) or a plasticizer (mixture). These additives are intended to prevent volatilization of the active compounds and crystallization or precipitation. They preferably replace 0.01 to 30% of the binder (based on 100% of the binder employed).

The plasticizers are from the chemical classes of the phthalic esters, such as dibutyl phthalate, dioctyl phthalate or benzylbutyl phthalate, the phosphoric esters, such as tributyl phosphate, the adipic esters, such as di-(2-ethylhexyl) adipate, the stearates, such as butyl stearate or amyl stearate, the oleates, such as butyl oleate, the glycerol ethers or relatively high-molecular-weight glycol ethers, glycerol esters and p-toluene-sulphonic esters.

Fixatives are chemically based on polyvinyl alkyl ethers, such as, for example, polyvinyl methyl ether, or ketones, such as benzophenone or ethylene benzophienone.

Particularly suitable as a solvent or diluent is also water, if appropriate as a mixture with one or more of the abovementioned organochemical solvents or diluents, emulsifiers and dispersants.

Particularly effective protection of wood is achieved by large-scale industrial impregnation processes, for example vacuum, double-vacuum or pressure processes.

If appropriate, the ready-to-use compositions can additionally comprise one or more other insecticides and, if appropriate, additionally one or more fungicides.

Suitable additional components which may be admixed are, preferably, the insecticides and fungicides mentioned in WO 94/29 268. The compounds mentioned in that document are expressly part of the present application.

Very particularly preferred components which may be admixed are insecticides, such as chlorpyriphos, phoxim, silafluofin, alphamethrin, cyfluthrin, cypermethrin, deltamethrin, permethrin, imidacloprid, NI-25, flufenoxuron, hexaflumuron and triflumuron, and fungicides, such as epoxyconazole, hexaconazole, azaconazole, propiconazole, tebuconazole, cyproconazole, metconazole, imazalil, dichlorofluanide, tolylfluanide, 3-iodo-2-propinyl-butyl carbamate, N-octyl-isothiazolin-3-one and 4,5-dichloro-N-octylisothiazolin-3-one.

The preparation and the use of the active compounds according to the invention can be seen from the examples below.

PREPARATION EXAMPLES
Example 1

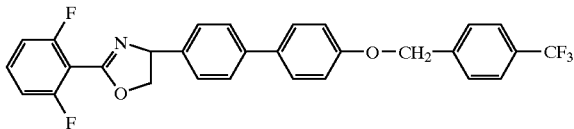

70.2 g (0.2 mol) of 2-(2,6-difluorophenyl)-4-(4'-hydroxybiphenyl-4-yl)-1,3-oxazoline and 30.4 g (0.22 mol) of potassium carbonate are suspended in 700 ml of acetonitrile and admixed with 0.1 ml of tris(3,6-dioxaheptyl) amine (TDA). Under reflux, 42.8 g (0.22 mol) of 4-trifluoromethylbenzyl chloride are then added dropwise, and the reaction mixture is stirred at this temperature for 14 hours. The mixture is subsequently concentrated by distilling off the solvent and the residue is taken up in 1 l of methylene chloride, washed with water, dried over sodium sulphate and concentrated.

82.7 g (81% of theory) of 2-(2,6-difluorophenyl)-4-[4'-(4"-trifluoromethylbenzyl-oxy)-biphenyl-4-yl]-1,3-oxazoline of melting point 166° C. are obtained.

Preparation of the Starting Material

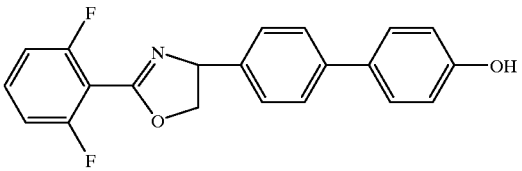

10.9 g (0.026 mol) of 2-(2,6-difluorophenyl)-4-(4'-ethoxycarbonyloxybiphenyl-4-yl)-1,3-oxazoline are suspended in 50 ml of methanol, and 35.4 ml (0.52 mol) of 25% strength aqueous ammonia solution are then added dropwise at room temperature. After 28 hours at room temperature, the precipitate is filtered off with suction and washed with a little methanol.

Yield 7.6 g (97.4% of theory), mp. 180 to 182° C.

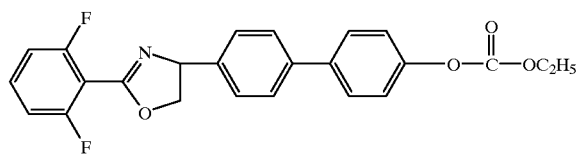

At 5° C., 4 ml (0.045 mol) of 50% strength aqueous sodium hydroxide solution are added dropwise to 19.8 g (0.043 mol) of 2-(2,6-difluorobenzoylamido)-2-(4'-ethoxy-carbonyloxybiphenyl-4-yl)-1-choroethane in 120 ml of dimethylformamide. After 2 hours at room temperature, the mixture is stirred into 500 ml of ice-water and the precipitated crystals are filtered off with suction.

Yield: 15.1 g (83% of theory), mp.: 98 to 100° C.

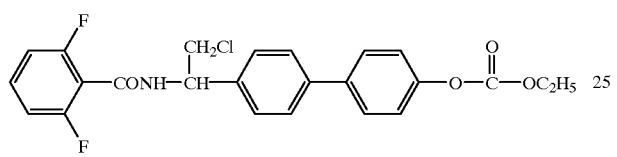

At 5° C., 130.4 g (0.98 mol) of aluminium chloride are introduced a little at a time over a period of 30 minutes into a mixture of 53 g (0.213 mol) of 2-(2,6-difluorobenzoyl-amido)-2-methoxy-1-chloroethane, 48.4 g (0.2 mol) of 4-ethoxycarbonyloxybiphenyl, and 12 ml of glacial acetic acid in 200 ml of methylene chloride. The colour of the reaction mixture turns blue and then red-violet. The reaction mixture is stirred for 1 hours at 5° C. and for 1 hour at 10° C. and then carefully poured onto ice, the suspension is carefully decanted off from water and concentrated using a rotary evaporator, the residue is admixed with 50 ml of acetonitrile and the precipitated crystals are filtered off with suction.

Yield 42.8 (47% of theory), mp. 209° C.

By the method of Example 1 and according to the general preparation procedures, the compounds of the formula (I) listed in Table 2 below are obtained:

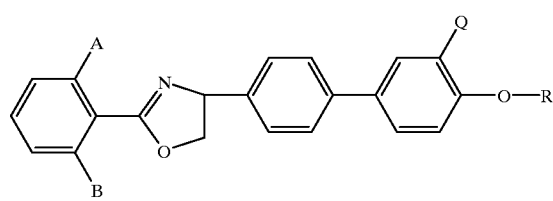

TABLE 2

| Ex. No. | A | B | Q | R | Mp (° C.) or logP[1] |
|---|---|---|---|---|---|
| 2 | Cl | H | H | —CH$_2$—C$_6$H$_4$—CF$_3$ | 135–37 |
| 3 | F | Cl | H | —CH$_2$C(CH$_3$)=N—O—CH(CH$_3$)C$_2$H$_5$ | 5.90 (A isomer)* 5.81 (B isomer)* |
| 4 | F | Cl | H | —C(CH$_3$)—C(CH$_3$)=N—O—C$_3$H$_7$-i | 6.30 |
| 5 | Br | H | H | —C$_3$H$_7$-i | 95–97 |
| 6 | F | F | H | —CO—NH—C$_3$H$_7$—i | 126–30 |
| 7 | F | F | H | —CF=CF—CH=CH$_2$ | 5.01 |
| 8 | F | F | H | —CH$_2$CH=NOCH$_3$ | 3.97 (A isomer)* 4.14 (B isomer)* |
| 9 | H | Cl | H | —C$_3$H$_7$—n | 80–85 |
| 10 | H | Cl | H | —CH$_2$—C$_6$H$_4$—C$_4$H$_9$-t | 165–70 |
| 11 | H | Cl | H | —C$_3$H$_7$—i | 80 |
| 12 | H | Cl | H | —C$_4$H$_9$-n | 80–84 |
| 13 | H | Cl | H | —CH$_2$—C$_6$H$_{11}$ | 112–14 |
| 14 | H | Cl | H | —CH$_2$C$_3$H$_7$-i | 87–95 |
| 15 | F | F | H | —CH$_2$CH$_2$—CH=CF$_2$ | 83 |
| 16 | F | F | H | —CH$_2$CH=NOC$_2$H$_5$ | 4.35 (A isomer)* 4.53 (B isomer)* |
| 17 | F | F | H | —CH$_2$—C$_6$H$_4$—F | 158–62 |

TABLE 2-continued

| Ex. No. | A | B | Q | R | Mp (° C.) or logP[1] |
|---|---|---|---|---|---|
| 18 | F | F | H | —CH₂—(2,3-dimethylphenyl) | 115–18 |
| 19 | F | F | H | —CH₂—(4-cyanophenyl) | 155–56 |
| 20 | F | F | H | —CH₂—(2,3-dichlorophenyl) | 124–26 |
| 21 | F | F | H | —CH₂—(4-OCF₃-phenyl) | 154–56 |
| 22 | I | H | H | —CH₂—(2,2-dichlorocyclopropyl) | 5.43 |
| 23 | F | F | H | —CH₂—(4-SCF₃-phenyl) | 86–95 |
| 24 | F | F | H | —CH₂—(2-fluorophenyl) | 130–35 |
| 25 | F | F | H | —CH₂—(3-fluorophenyl) | 135–36 |
| 26 | F | F | H | —CH₂—(3-COOCH₃-phenyl) | 120–22 |
| 27 | F | Cl | H | —C₃H₇—i | 108–10 |
| 28 | F | F | — | cyclopentyl-H | 125–26 |
| 29 | F | Cl | H | —C₃H₇—n | 130–32 |
| 30 | F | Cl | H | —CH₂—C₃H₇—i | 122 |
| 31 | F | F | H | —CH₂—(4-SO₂CH₃-phenyl) | 165 |

TABLE 2-continued

| Ex. No. | A | B | Q | R | Mp (° C.) or logP[1] |
|---|---|---|---|---|---|
| 32 | F | F | H | 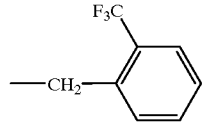 -CH₂-(2-CF₃-C₆H₄) | 88–90 |
| 33 | F | F | H | 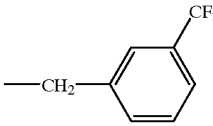 -CH₂-(3-CF₃-C₆H₄) | 118 |
| 34 | F | Cl | H | —C₄H₉-n | 95–105 |
| 35 | F | F | H | —CH(CH₃)—CH=NOCH₃ | |
| 36 | F | F | H | —CH(CH₃)—C≡CH | 4.15 |
| 37 | Cl | H | H | —CH(CH₃)—C≡CH | 4.49 |
| 38 | Cl | F | H | 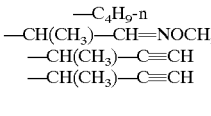 —CO—O—(2-F-6-Cl-C₆H₃) | 99–102 |
| 39 | Cl | H | H | —CH₂—C₃H₇—i | 72–75 |
| 40 | Cl | Cl | H | 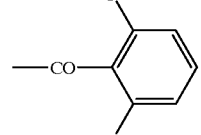 —CH₂-(4-CF₃-C₆H₄) | 193–94 |
| 41 | Cl | Cl | H | —C₃H₇—i | 122–23 |
| 42 | F | F | H | 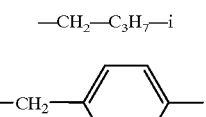 —CH₂—C(=N—OC₂H₅)—C(CH₃)₂—C(=CCl₂) | 6.48 (A isomer)* 6.37 (B isomer)* |
| 43 | F | F | Cl | 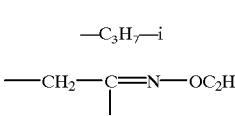 —CH(CH₃)—C(CH₃)=N—OC₃H₇ | 5.99 (A isomer)* 5.85 (B isomer)* |
| 44 | F | F | Cl | 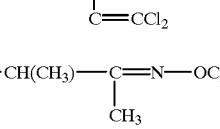 —CH(CH₃)—C(CH₃)=NOH | 3.95 (A isomer)* 3.89 (B isomer)* |
| 45 | Cl | H | Cl | 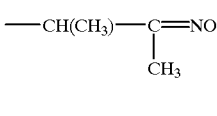 —CH(CH₃)—C(CH₃)=NOH | 4.33 (A isomer)* 4.26 (B isomer)* |
| 46 | F | F | H | 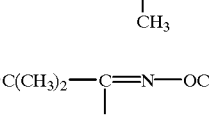 —C(CH₃)₂—C(CH₃)=N—OC₃H₇-i | 6.00 |
| 47 | F | Cl | H | 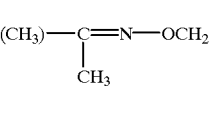 —CH(CH₃)—C(CH₃)=N—OCH₂—C₃H₇-i | 6.24 (A isomer)* 6.10 (B isomer)* |
| 48 | F | Cl | H | 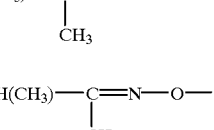 —CH(CH₃)—C(CH₃)=N—O—CH(CH₃)C₂H₅ | 6.27 (A isomer)* 6.13 (B isomer)* |
| 49 | F | Cl | H |  —CH(CH₃)—C(CH₃)=N—O—C₄H₉-n | 6.23 (A isomer)* 6.09 (B isomer)* |

TABLE 2-continued

| Ex. No. | A | B | Q | R | Mp (° C.) or logP[1)] |
|---|---|---|---|---|---|
| 50 | F | F | H | —CH(CH$_3$)—C(CH$_3$)=N—O—CH(CH$_3$)C$_2$H$_5$ | 5.99 (A isomer)*<br>5.84 (B isomer)* |
| 51 | F | F | H | —CH(CH$_3$)—C(CH$_3$)=N—O—CH$_2$—C$_3$H$_7$-$i$ | 5.93 (A isomer)*<br>5.79 (B isomer)* |
| 52 | F | F | H | —CH(CH$_3$)—C(CH$_3$)=N—OC$_4$H$_9$-$n$ | 5.94 (A isomer)*<br>5.80 (B isomer)* |
| 53 | F | F | H | —C(CH$_3$)$_2$—CH=NOC$_2$H$_5$ | 5.00 |
| 54 | F | Cl | H | —CH$_2$—C(CH$_3$)=N—OCH$_2$—C$_3$H$_7$-$i$ | 5.85 (A isomer)*<br>5.76 (B isomer)* |
| 55 | F | F | H | —CH$_2$—C(CH$_3$)=N—OC$_4$H$_9$-$n$ | 5.58 (A isomer)*<br>5.51 (B isomer)* |
| 56 | F | F | H | —CH$_2$—C(CH$_3$)=N—O—CH(CH$_3$)C$_2$H$_5$ | 5.61 (A isomer)*<br>5.54 (B isomer)* |
| 57 | F | F | H | —C(CH$_3$)$_2$—CH=NOCH$_3$ | 4.62 |
| 58 | Cl | H | H | —C(CH$_3$)$_2$—C(CH$_3$)=N—OC$_3$H$_7$-$i$ | 6.44 |
| 59 | F | F | H | —C(CH$_3$)$_2$—C(CH$_3$)=N—O—CH(CH$_3$) | 6.43 |
| 60 | F | F | H | —C(CH$_3$)$_2$—C(CH$_3$)=N—O—C$_4$H$_9$-$n$ | 6.38 |
| 61 | Cl | H | Cl | —CH(CH$_3$)—C(CH$_3$)=N—O—C$_4$H$_9$-$n$ | 6.84 (A isomer)*<br>6.67 (B isomer)* |
| 62 | Cl | H | Cl | —CH(CH$_3$)—C(CH$_3$)=N—O—CH(CH$_3$)C$_2$H$_5$ | 6.89 (A isomer)*<br>6.71 (B isomer)* |
| 63 | F | F | Cl | —CH(CH$_3$)—C(CH$_3$)=N—O—C$_4$H$_9$-$n$ | 6.37 (A isomer)*<br>6.22 (B isomer)* |
| 64 | F | F | Cl | —CH(CH$_3$)—C(CH$_3$)=N—O—CH(CH$_3$)C$_2$H$_5$ | 6.41 (A isomer)*<br>6.26 (B isomer)* |
| 65 | Cl | Cl | H | —CH(CH$_3$)—COCH$_3$ | 108–10 |
| 66 | Cl | Cl | H | —CH(CH$_3$)—C(CH$_3$)=N—OCH$_3$ | 5.27 (A isomer)*<br>5.17 (B isomer)* |
| 67 | Cl | Cl | H | —CH(CH$_3$)—C(CH$_3$)=N—OC$_2$H$_5$ | 5.69 (A isomer)*<br>5.57 (B isomer)* |

TABLE 2-continued

| Ex. No. | A | B | Q | R | Mp (° C.) or logP[1] |
|---|---|---|---|---|---|
| 68 | Br | H | H | —CH($CH_3$)—COCH$_3$ | 4.13 |
| 69 | Cl | H | H | $CF_3$ | 58–60 |
| 70 | $CH_3O$— | H | H | $CF_3$ | 50–54 |
| 71 | $CF_3$ | H | H | $CF_3$ | 63–65 |
| 72 | $CH_3SO_2$— | H | H | $CF_3$ | 128–32 |
| 73 | $C_2H_5O$— | H | H | $CF_3$ | 68 |
| 74 | i-$C_3H_7O$— | H | H | $CF_3$ | 84 |
| 75 | $NO_2$ | H | H | $CF_3$ | 75–77 |
| 76 | $CH_3O$- | F | H | $CF_3$ | 4.49 |
| 77 | F | $NH_2$ | H | $CF_3$ | 93–95 |
| 78 | $CH_3S$- | H | H | $CF_3$ | 126–27 |
| 79 | i-$C_3H_7S$— | H | H | $CF_3$ | 98–102 |
| 80 | $C_2H_5S$— | H | H | $CF_3$ | 88 |
| 81 | $C_2H_5O$— | F | H | $CF_3$ | 98–100 |
| 82 | $C_2H_5CH(CH_3)O$— | F | H | $CF_3$ | 5.47 |
| 83 | $C_2H_5CH(CH_3)O$— | $C_2H_5CH(CH_3)O$— | H | $CF_3$ | 92–93 |
| 84 | i-$C_3H_7CH_2O$— | F | H | $CF_3$ | 5.57 |
| 85 | i-$C_3H_7CH_2O$— | i-$C_3H_7CH_2O$— | H | $CF_3$ | 93–95 |
| 86 | $C_2H_5$ | H | H | $CF_3$ | 5.78 |
| 87 |  | H | H | $CF_3$ | 5.47 |
| 88 | $CH_3O$ | H | H | $C_3H_7$-i | 50 |
| 89 | Br | H | H | $CF_3$ | 52-54 |
| 90 | I | H | H | $CF_3$ | 80-82 |
| 91 | Br | H | H | —CH($CH_3$)—CH(OH)$CH_3$ | 3.74 |
| 92 | Br | H | H | —CH($CH_3$)—C($CH_3$)=NOCH$_3$ | 5.08 (A isomer)* <br> 5.18 (B isomer)* |
| 93 | I | H | H | $C_3H_7$-i | 88–90 |
| 94 | I | H | H | 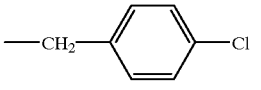 | 172–75 |
| 95 | Br | H | H | —$CH_2$—CH=$CH_2$ | 76–79 |
| 96 | Br | H | H | —$CH_2$—C≡CH | |
| 97 | F | H | Cl | 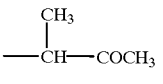 | 4.32 |
| 98 | F | H | Cl | 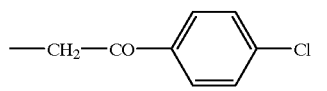 | 155–57 |
| 99 | F | Cl | H | 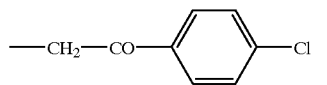 | 165–67 |
| 100 | F | H | H | —CH($CH_3$)—COCH$_3$ | 3.79 |
| 101 | F | H | H | 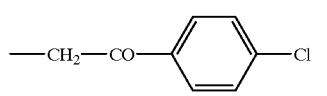 | 4.57 |
| 102 | F | F | H | —C($CH_3$)$_2$—CHO | 4.08 |

TABLE 2-continued

| Ex. No. | A | B | Q | R | Mp (° C.) or logP[1] |
|---|---|---|---|---|---|
| 103 | F | H | Cl | —CH$_2$—C(=NOCH$_3$)—(4-Cl-C$_6$H$_4$) 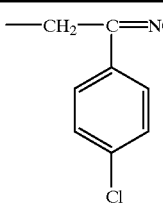 | 4.91 |
| 104 | F | Cl | H | —CH$_2$—C(=NOCH$_3$)—(4-Cl-C$_6$H$_4$) 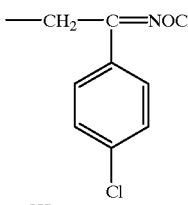 | 5.52 |
| 105 | F | H | Cl | —CH(CH$_3$)—C(CH$_3$)=NOCH$_3$ | 5.15 |
| 106 | F | H | Cl | —CH(CH$_3$)—C(CH$_3$)=NOC$_2$H$_5$ | 5.57 |
| 107 | F | H | H | —C$_3$H$_7$—i | 4.65 |
| 108 | F | H | H | —CH$_2$—C$_3$H$_7$—i | 5.34 |
| 109 | F | H | H | —CH$_2$—C(=NOCH$_3$)—(4-Cl-C$_6$H$_4$) 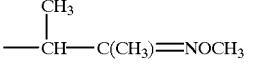 | 5.65 |
| 110 | F | H | H | —CH(CH$_3$)—C(CH$_3$)=NOCH$_3$ | 4.94 |
| 111 | F | H | H | —CH(CH$_3$)—C(CH$_3$)=NOC$_2$H$_5$ | 5.24 |
| 112 | F | Cl | H | —CH$_2$—CH=NOCH$_3$ | 4.27 |
| 113 | F | Cl | H | —CH$_2$—CH=NOC$_2$H$_5$ | 4.65 |
| 114 | F | F | Cl | —CH$_2$—CH=NOCH$_3$ | 4.33 |
| 115 | F | F | Cl | —CH$_2$—CH=NOC$_2$H$_5$ | 4.71 |
| 116 | Cl | H | Cl | —CH$_2$—CH=NOCH$_3$ | 4.72 |
| 117 | Cl | H | Cl | —CH$_2$—CH=NOC$_2$H$_5$ | 5.08 |
| 118 | F | H | Cl | —CH$_2$CF$_3$ | 115 |
| 119 | F | F | CH$_3$ | —CH$_2$CF$_3$ | 4.80 |
| 120 | CF$_3$CH$_2$O— | F | CH$_3$ | —CH$_2$CF$_3$ | 4.91 |
| 121 | Cl | H | —CH$_2$—CH=CH$_2$ | —CH$_2$CF$_3$ | 84 |
| 122 | Cl | H | CH$_3$ | —CH$_2$CF$_3$ | 55–87 |
| 123 | F | F | C$_2$H$_5$ | —CH$_2$CF$_3$ | 88–90 |
| 124 | Cl | H | H | —CH$_2$CF$_3$ | 62–66 |
| 125 | F | F | H | —CH$_2$—CF$_2$—(2,4-Cl$_2$-C$_6$H$_3$) 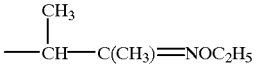 | 5.68 |
| 126 | F | F | H | —CH$_2$—CF$_2$—CHF$_2$ | |
| 127 | F | F | H | —(CH$_2$)$_3$—CF$_2$—CF$_3$ | |

[1]log p: Logarithm to base 10 of the n-octanol/water partition coefficient, determined by reversed phase HPLC analysis using H$_2$O/CH$_3$CN
*) A and B isomer: possible geometric isomers By the method of Example 1 (cf. the preparation of the starting material) and according to the general preparation procedures, the following compound (II-I) is obtained:

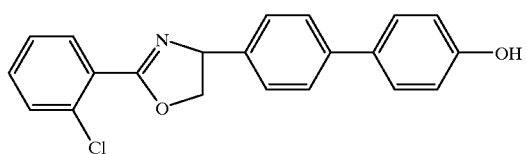

(II-I)

Mp.: 178–180° C.

USE EXAMPLES

In the Use Examples below, the compounds of the formulae (A) and (B)

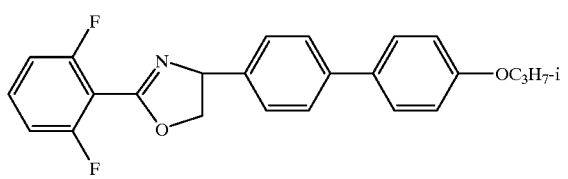

(A)

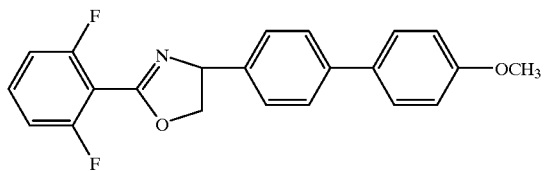

(B)

known from EP-A 0 432 661 were used as comparative substances.

Example A
*Heliothis armigera* Test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Soy shoots (*Glycine max*) are treated by being dipped into the active compound preparation of the desired concentration and are populated with caterpillars of the cotton bollworm (*Heliothis armigera*), while the leaves are still moist.

After the desired period of time, the activity in % is determined. 100% means that all the caterpillars have been killed; 0% means that none of the caterpillars have been killed.

In this test, at an exemplary active compound concentration of 0.00016% and in each case after 6 days, for example the compounds of Preparation Examples 1 and 3 caused a kill of 100% and the compound of Preparation Example 2 of 65%, whereas the known compound (A) effected a kill of only 10%.

Example B
Panonychus Test (resistant)

Solvent: 3 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Plum trees (*Prunus domestica*) of a height of about 30 cm which are heavily infested by all stages of the fruit tree red spider mite (*Panonychus ulmi*) are sprayed with an active compound preparation of the desired concentration.

After the desired period of time, the activity in % is determined. 100% means that all spider mites have been killed; 0% means that none of the spider mites have been killed.

In this test, at an exemplary active compound concentration of 0.00016% and in each case after 14 days, for example the compound of Preparation Example caused a kill of 95%, whereas the known compound (A) effected a kill of only 50%.

Example C
Phaedon Larvae Test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the active compound preparation of the desired concentration and are populated with larvae of the mustard beetle (*Phaedon cochleariae*), while the leaves are still moist.

After the desired period of time, the kill in % is determined. 100% means that all the beetle larvae have been killed; 0% means that none of the beetle larvae have been killed.

In this test, for example a) the compound of Preparation Example 4, at an exemplary active compound concentration of 0.00001% and in each case after 7 days, caused a kill of 100%, whereas the known compound (A) effected a kill of only 55% and b) the compounds of Preparation Examples 1, 2 and 3, at an exemplary active compound concentration of 0.01% and in each case after 7 days, caused a kill of 100%, whereas the known compound (B) showed no activity.

Example D
Plutella Test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the active compound preparation of the desired concentration and are infested with caterpillars of the diamond back moth (*Plutella xylostella*), while the leaves are still moist.

After the desired period of time, the activity in % is determined. 100% means that all caterpillars have been killed; 0% means that none of the caterpillars have been killed.

In this test, at an exemplary active compound concentration of 0.000032% and in each case after 7 days, for example the compounds of Preparation Examples 1 and 3 caused a kill of 85% and 100%, respectively, whereas the known compound (B) showed no activity.

Example E

Spodoptera exigua Test

Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (Brassica oleracea) are treated by being dipped into the active compound preparation of the desired concentration and populated with caterpillars of the owlet moth (Spodoptera exigua), while the leaves are still moist.

After the desired period of time, the activity in % is determined. 100% means that all caterpillars have been killed; 0% means that none of the caterpillars have been killed.

In this test, at an exemplary active compound concentration of 0.000032% and in each case after 6 days, for example the compounds of Preparation Examples 1 and 2 caused a kill of 80%, whereas the known compound (A) showed no activity.

Example F

Spodoptera frugiperda Test

Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (Brassica oleracea) are treated by being dipped into the active compound preparation of the desired concentration and populated with caterpillars of the owlet moth (Spodoptera frugiperda) while the leaves are still moist.

After the desired period of time, the activity in % is determined. 100% means that all caterpillars have been killed; 0% means that none of the caterpillars have been killed.

In this test, at an exemplary active compound concentration of 0.0001% and in each case after 7 days, for example the compounds of Preparation Examples 1, 2, 3 and 4 caused a kill of 100%, whereas the known compound (B) showed no activity and the known compound (A) effected a kill of only 30%.

Example G

Tetranychus Test (OP resistant/spray treatment)

Solvent: 3 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Bean plants (Phaseolus vulgaris) which are heavily infested by all stages of the greenhouse red spider mite (Tetranychus urticae) are sprayed with an active compound preparation of the desired concentration.

After the desired period of time, the activity in % is determined. 100% means that all the spider mites have been killed; 0% means that none of the spider mites have been killed.

In this test, at an exemplary active compound concentration of 0.000032% and in each case after 14 days, for example the compound of Preparation Example 1 caused a kill of 98%, whereas the known compound (A) effected a kill of only 50%.

Example H

Cockroach Test

Test animals: Periplaneta americana
Solvent: Dimethyl sulphoxide 20 mg of active compound are dissolved in 1 ml of dimethyl sulphoxide, and lower concentrations are prepared by dilution with distilled water.

For one minute, 4 test animals are dipped into the active compound preparation to be tested. The animals are transferred into plastic beakers and kept for 7 days in a climatized room, after which the kill is determined.

100% means that all cockroaches have been killed; 0% means that none of the cockroaches have been killed.

In this test, at an exemplary active compound concentration of 100 ppm, for example the compound of Preparation Example 2 caused a kill of 100%.

Example I

Blowfly Larvae Test/development-inhibitory Action

Test animals: Lucilia cuprina larvae
Solvent: Dimethyl sulphoxide 20 m of active compound are dissolved in 1 ml of dimethyl sulphoxide, and lower concentrations are prepared by dilution with distilled $H_2O$.

About 20 Lucilia cuprina larvae are placed in a test tube containing about 1 $cm^3$ of horsemeat and 0.5 ml of the active compound preparation to be tested. The activity of the active compound preparation is determined after 24 hours and 48 hours. The test tubes are transferred into beakers whose bottom is covered with sand. After a further 2 days, the test tubes are removed and the pupae are counted.

The activity of the active compound preparation is judged by the number of flies which have hatched after 1.5 times the development period of an untreated control. 100% means that no flies have hatched; 0% means that all flies have hatched normally.

In this test, at an exemplary active compound concentration of 100 ppm, for example the compounds of Preparation Examples 2 and 5 each had an activity of 100%.

What is claimed is:

1. Compounds 1–8, 10–11, 13, 15–26, 28 and 30–127 of the formula (I)

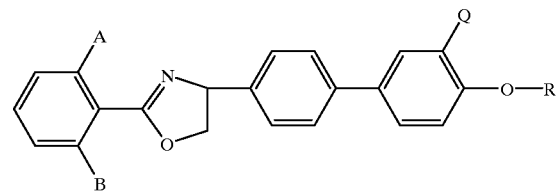

(I)

in which the radicals A, B, Q and R are each as defined in Table 1 below:

TABLE 1

| Compound No. | A | B | Q |
|---|---|---|---|
| 1 | F | F | H |
| 2 | Cl | H | H |
| 3 | F | Cl | H |
| 4 | F | Cl | H |
| 5 | Br | H | H |
| 6 | F | F | H |
| 7 | F | F | H |
| 8 | F | F | H |
| 10 | H | Cl | H |
| 11 | H | Cl | H |
| 13 | H | Cl | H |
| 15 | F | F | H |
| 16 | F | F | H |
| 17 | F | F | H |
| 18 | F | F | H |
| 19 | F | F | H |
| 20 | F | F | H |
| 21 | F | F | H |
| 22 | I | H | H |
| 23 | F | F | H |
| 24 | F | F | H |
| 25 | F | F | H |
| 26 | F | F | H |
| 28 | F | F | H |
| 30 | F | Cl | H |
| 31 | F | F | H |
| 32 | F | F | H |
| 33 | F | F | H |
| 34 | F | Cl | H |
| 35 | F | F | H |
| 36 | F | F | H |
| 37 | Cl | H | H |
| 38 | Cl | F | H |
| 39 | Cl | H | H |
| 40 | Cl | Cl | H |
| 41 | Cl | Cl | H |
| 42 | F | F | H |
| 43 | F | F | Cl |
| 44 | F | F | Cl |
| 45 | Cl | H | Cl |
| 46 | F | F | H |
| 47 | F | Cl | H |
| 48 | F | Cl | H |
| 49 | F | Cl | H |
| 50 | F | F | H |
| 51 | F | F | H |
| 52 | F | F | H |
| 53 | F | F | H |
| 54 | F | Cl | H |
| 55 | F | F | H |
| 56 | F | F | H |
| 57 | F | F | H |
| 58 | Cl | H | H |
| 59 | F | F | H |
| 60 | F | F | H |
| 61 | Cl | H | Cl |
| 62 | Cl | H | Cl |
| 63 | F | F | Cl |
| 64 | F | F | Cl |
| 65 | Cl | Cl | H |
| 66 | Cl | Cl | H |
| 67 | Cl | Cl | H |
| 68 | Br | H | H |
| 69 | Cl | H | H |
| 70 | CH$_3$O— | H | H |
| 71 | CF$_3$ | H | H |
| 72 | CH$_3$SO$_2$— | H | H |
| 73 | C$_2$H$_5$O— | H | H |
| 74 | i-C$_3$H$_7$O— | H | H |
| 75 | NO$_2$ | H | H |
| 76 | CH$_3$O— | F | H |
| 77 | F | NH$_2$ | H |
| 78 | CH$_3$S— | H | H |
| 79 | i-C$_3$H$_7$S— | H | H |
| 80 | C$_2$H$_5$S— | H | H |
| 81 | C$_2$H$_5$O— | F | H |
| 82 | C$_2$H$_5$CH(CH$_3$)O— | F | H |
| 83 | C$_2$H$_5$CH(CH$_3$)O— | C$_2$H$_5$CH(CH$_3$)O— | H |
| 84 | i-C$_3$H$_7$CH$_2$O— | F | H |
| 85 | i-C$_3$H$_7$CH$_2$O— | i-C$_3$H$_7$CH$_2$O— | H |
| 86 | C$_2$H$_5$ | H | H |
| 87 | C$_6$H$_5$ (phenyl) | H | H |
| 88 | CH$_3$O | H | H |
| 89 | Br | H | H |
| 90 | I | H | H |
| 91 | Br | H | H |
| 92 | Br | H | H |
| 93 | I | H | H |
| 94 | I | H | H |
| 95 | Br | H | H |
| 96 | Br | H | H |
| 97 | F | H | Cl |
| 98 | F | H | Cl |
| 99 | F | Cl | H |
| 100 | F | H | H |
| 101 | F | H | H |
| 102 | F | F | H |
| 103 | F | H | Cl |
| 104 | F | Cl | H |
| 105 | F | H | Cl |
| 106 | F | H | Cl |
| 107 | F | H | H |
| 108 | F | H | H |
| 109 | F | H | H |
| 110 | F | H | H |
| 111 | F | H | H |
| 112 | F | Cl | H |
| 113 | F | Cl | H |
| 114 | F | F | Cl |
| 115 | F | F | Cl |
| 116 | Cl | H | Cl |
| 117 | Cl | H | Cl |
| 118 | F | H | H |
| 119 | F | F | CH$_3$ |
| 120 | CF$_3$CH$_2$O— | F | CH$_3$ |
| 121 | Cl | H | —CH$_2$—CH=CH$_2$ |
| 122 | Cl | H | CH$_3$ |
| 123 | F | F | C$_2$H$_5$ |
| 124 | Cl | H | H |
| 125 | F | F | H |
| 126 | F | F | H |
| 127 | F | F | H |

| Compound No. | R |
|---|---|
| 1 | —CH$_2$—C$_6$H$_4$—CF$_3$ |
| 2 | —CH$_2$—C$_6$H$_4$—CF$_3$ |
| 3 | —CH$_2$—C(CH$_3$)=N—O—CH(CH$_3$)C$_2$H$_5$ |
| 4 | —C(CH$_3$)$_2$—C(CH$_3$)=N—O—C$_3$H$_7$-i |
| 5 | —C$_3$H$_7$-i |
| 6 | —CO—NH—C$_3$H$_7$-i |
| 7 | —CF=CF—CH=CH$_2$ |
| 8 | —CH$_2$—CH=NOCH$_3$ |

TABLE 1-continued

| | |
|---|---|
| 10 | —CH₂—C₆H₄—C₄H₉-t (para) |
| 11 | —C₃H₇-i |
| 13 | —CH₂—C₆H₁₁ (H) |
| 15 | —CH₂CH₂—CH=CF₂ |
| 16 | —CH₂—CH=NOC₂H₅ |
| 17 | —CH₂—C₆H₄—F (para) |
| 18 | —CH₂—C₆H₃(CH₃)₂ (3,4-dimethyl) |
| 19 | —CH₂—C₆H₄—CN (para) |
| 20 | —CH₂—C₆H₃Cl₂ (2,3-dichloro) |
| 21 | —CH₂—C₆H₄—OCF₃ (para) |
| 22 | —CH₂—cyclopropyl(2,2-Cl₂) |
| 23 | —CH₂—C₆H₄—SCF₃ (para) |
| 24 | —CH₂—C₆H₄—F (ortho) |
| 25 | —CH₂—C₆H₄—F (meta) |

TABLE 1-continued

| | |
|---|---|
| 26 | —CH₂—C₆H₄—COOCH₃ (meta) |
| 28 | cyclopentyl (H) |
| 30 | —CH₂—C₃H₇-i |
| 31 | —CH₂—C₆H₄—SO₂CH₃ (para) |
| 32 | —CH₂—C₆H₄—CF₃ (ortho) |
| 33 | —CH₂—C₆H₄—CF₃ (meta) |
| 34 | —C₄H₉-n |
| 35 | —CH(CH₃)—CH=NOCH₃ |
| 36 | —CH(CH₃)—C≡CH |
| 37 | —CH(CH₃)—C≡CH |
| 38 | —CO—C₆H₃(F)(Cl) (2-F, 6-Cl) |
| 39 | —CH₂—C₃H₇-i |
| 40 | —CH₂—C₆H₄—CF₃ (para) |
| 41 | —C₃H₇-i |
| 42 | —CH₂—C(=N—OC₂H₅)—C(CH₃)₂—C(=CCl₂) |
| 43 | —CH(CH₃)—C(CH₃)=N—OC₃H₇ |
| 44 | —CH(CH₃)—C(CH₃)=NOH |
| 45 | —CH(CH₃)—C(CH₃)=NOH |

TABLE 1-continued

| | |
|---|---|
| 46 | —C(CH₃)₂—C(CH₃)=N—OC₃H₇-i |
| 47 | —CH(CH₃)—C(CH₃)=N—OCH₂—C₃H₇-i |
| 48 | —CH(CH₃)—C(CH₃)=N—O—CH(CH₃)C₂H₅ |
| 49 | —CH(CH₃)—C(CH₃)=N—O—C₄H₉-n |
| 50 | —CH(CH₃)—C(CH₃)=N—O—CH(CH₃)C₂H₅ |
| 51 | —CH(CH₃)—C(CH₃)=N—O—CH₂—C₃H₇-i |
| 52 | —CH(CH₃)—C(CH₃)=N—OC₄H₉-n |
| 53 | —C(CH₃)₂—CH=NOC₂H₅ |
| 54 | —CH₂—C(CH₃)=N—OCH₂—C₃H₇-i |
| 55 | —CH₂—C(CH₃)=N—OC₄H₉-n |
| 56 | —CH₂—C(CH₃)=N—O—CH(CH₃)C₂H₅ |
| 57 | —C(CH₃)₂—CH=NOCH₃ |
| 58 | —C(CH₃)₂—C(CH₃)=N—OC₃H₇-i |
| 59 | —C(CH₃)₂—C(CH₃)=N—O—CH(CH₃)C₂H₅ |
| 60 | —C(CH₃)₂—C(CH₃)=N—O—C₄H₉-n |
| 61 | —CH(CH₃)—C(CH₃)=N—O—C₄H₉-n |
| 62 | —CH(CH₃)—C(CH₃)=N—O—CH(CH₃)C₂H₅ |
| 63 | —CH(CH₃)—C(CH₃)=N—O—C₄H₉-n |

TABLE 1-continued

| | |
|---|---|
| 64 | —CH(CH₃)—C(CH₃)=N—O—CH(CH₃)C₂H₅ |
| 65 | —CH(CH₃)—COCH₃ |
| 66 | —CH(CH₃)—C(CH₃)=N—OCH₃ |
| 67 | —CH(CH₃)—C(CH₃)=N—OC₂H₅ |
| 68 | —CH(CH₃)—COCH₃ |
| 69 | CF₃ |
| 70 | CF₃ |
| 71 | CF₃ |
| 72 | CF₃ |
| 73 | CF₃ |
| 74 | CF₃ |
| 75 | CF₃ |
| 76 | CF₃ |
| 77 | CF₃ |
| 78 | CF₃ |
| 79 | CF₃ |
| 80 | CF₃ |
| 81 | CF₃ |
| 82 | CF₃ |
| 83 | CF₃ |
| 84 | CF₃ |
| 85 | CF₃ |
| 86 | CF₃ |
| 87 | CF₃ |
| 88 | C₃H₇-i |
| 89 | CF₃ |
| 90 | CF₃ |
| 91 | —CH(CH₃)—CH(OH)CH₃ |
| 92 | —CH(CH₃)—C(CH₃)=NOCH₃ |
| 93 | C₃H₇-i |
| 94 | —CH₂—C₆H₄—Cl |
| 95 | —CH₂—CH=CH₂ |
| 96 | —CH₂—C≡CH |
| 97 | —CH(CH₃)—COCH₃ |
| 98 | —CH₂—CO—C₆H₄—Cl |
| 99 | —CH₂—CO—C₆H₄—Cl |
| 100 | —CH(CH₃)—COCH₃ |
| 101 | —CH₂—CO—C₆H₄—Cl |
| 102 | —C(CH₃)₂—CHO |

TABLE 1-continued

| | |
|---|---|
| 103 | —CH₂—C(=NOCH₃)—(4-Cl-C₆H₄) |
| 104 | —CH₂—C(=NOCH₃)—(4-Cl-C₆H₄) |
| 105 | —CH(CH₃)—C(CH₃)=NOCH₃ |
| 106 | —CH(CH₃)—C(CH₃)=NOC₂H₅ |
| 107 | —C₃H₇-i |
| 108 | —CH₂—C₃H₇-i |
| 109 | —CH₂—C(=NOCH₃)—(4-Cl-C₆H₄) |
| 110 | —CH(CH₃)—C(CH₃)=NOCH₃ |
| 111 | —CH(CH₃)—C(CH₃)=NOC₂H₅ |

TABLE 1-continued

| | |
|---|---|
| 112 | —CH₂—CH=NOCH₃ |
| 113 | —CH₂—CH=NOC₂H₅ |
| 114 | —CH₂—CH=NOCH₃ |
| 115 | —CH₂—CH=NOC₂H₅ |
| 116 | —CH₂—CH=NOCH₃ |
| 117 | —CH₂—CH=NOC₂H₅ |
| 118 | —CH₂CF₃ |
| 119 | —CH₂CF₃ |
| 120 | —CH₂CF₃ |
| 121 | —CH₂CF₃ |
| 122 | —CH₂CF₃ |
| 123 | CH₂CF₃ |
| 124 | —CH₂CF₃ |
| 125 | —CH₂—CF₂—(2,4-Cl₂-C₆H₃) |
| 126 | —CH₂—CF₂—CHF₂ |
| 127 | —(CH₂)₃—CF₂—CF₃. |

2. Compound of the formula

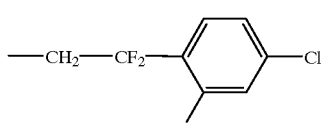

3. Compound of the formula

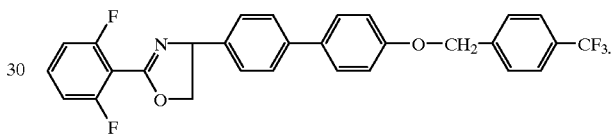

4. Compound of the formula

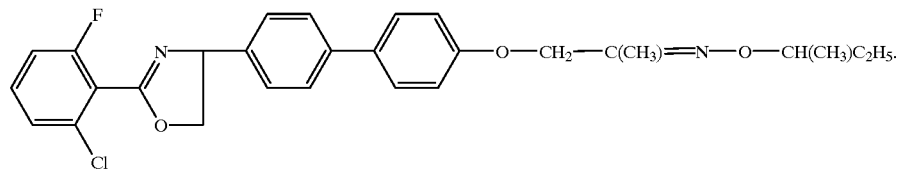

5. Compound of the formula

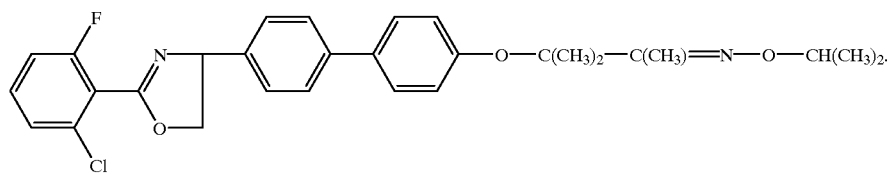

6. Compound of the formula

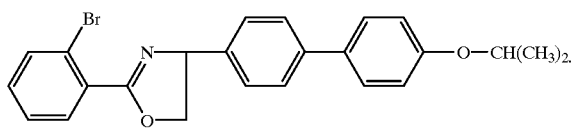

7. Compound of the formula (II-1)

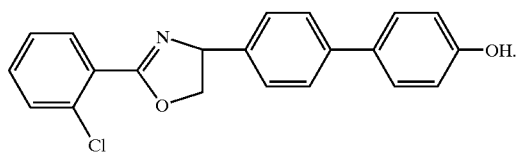

8. A pesticidal composition, comprising at least one compound of the formula (I) according to claim 1 and one or more extenders and/or surfactants.

9. A method for controlling pests, comprising the step of allowing a compound of the formula (I) according to claim 1 to act on pests and/or their habitats.

10. A process for preparing a pesticidal composition, comprising the step of mixing a compound of the formula (I) according to claim 1 with extenders and/or surfactants.

11. A process for preparing a compound of the formula (I) according to claim 1, comprising the step of reacting a compound of the formula (II)

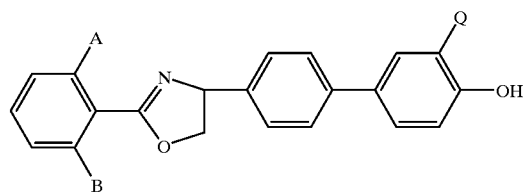

wherein
A, B and Q are each as defined in claim 1,
with a compound of the formula (III)

M—R          (III)

wherein
R is as defined in claim 1, and
M represents a leaving group.

12. The process of claim 11 wherein the reaction is carried out in the presence of a base.

13. The process of claim 11 wherein the reaction is carried out in the presence of a catalyst.

14. The process of claim 11 wherein the reaction is carried out in the presence of a base and a catalyst.

15. The process of claim 11 wherein the reaction is carried out in the presence of a diluent.

16. The process of claim 11 wherein the reaction is carried out in the presence of a base and a diluent.

17. The process of claim 11 wherein the reaction is carried out in the presence of a catalyst and a diluent.

18. The process of claim 11 wherein the reaction is carried out in the presence of a base, catalyst, and diluent.

19. A process for preparing a compound of the formula (I) according to claim 1, comprising the step of cyclizing a compound of the formula (XVII)

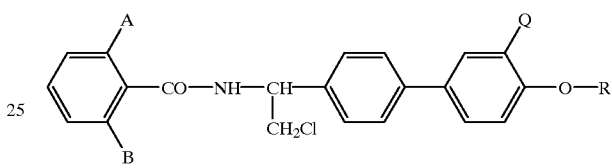

wherein
A, B, Q and R are each as defined in claim 1,
in the presence of a base, at a temperature between 0° C. and 100° C.

20. The process of claim 19 wherein the base is sodium hydroxide.

21. The process of claim 19 wherein the reaction is carried out in the presence of a phase-transfer catalyst.

22. The process of claim 21 wherein the phase-transfer catalyst is an ammonium compound.

23. The process of claim 19 wherein the reaction is carried out in the presence of a diluent.

24. The process of claim 23 wherein the diluent is dimethylformamide.

25. The process of claim 19 wherein the reaction is carried out in the presence of a diluent and a phase-transfer catalyst.

26. A pesticidal composition, comprising:
   a) an ingredient selected from extenders, surfactants and mixtures thereof, and
   b) one or more compounds selected from the group consisting of:

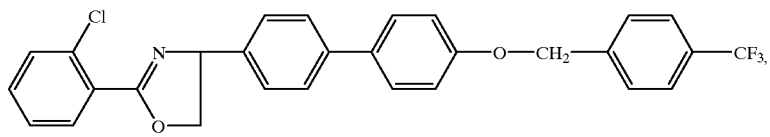

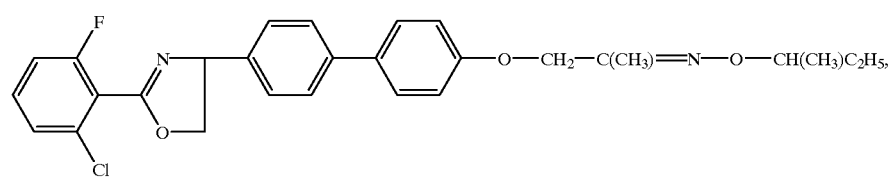

-continued

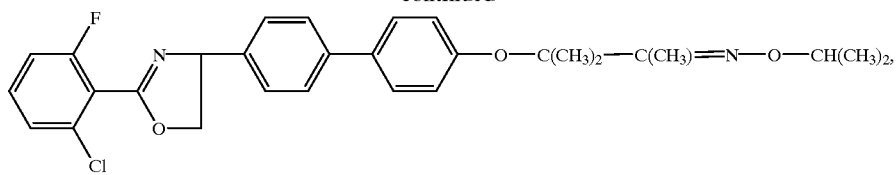

and

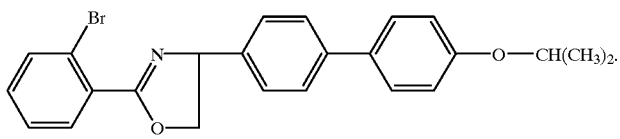

27. A process for preparing a substituted oxazoline derivative, comprising the step of cyclizing a compound of the formula (XVII)

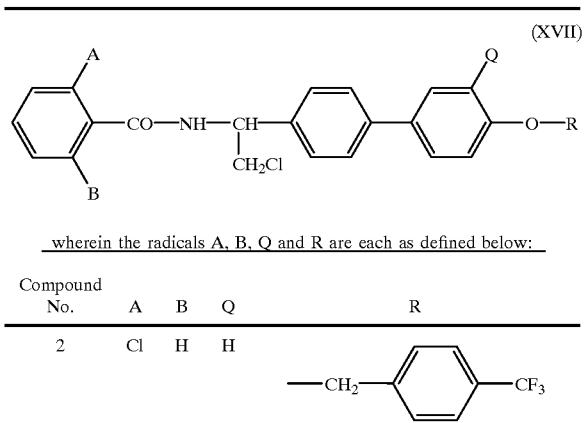

wherein the radicals A, B, Q and R are each as defined below:

| Compound No. | A | B | Q | R |
|---|---|---|---|---|
| 2 | Cl | H | H | —CH$_2$—C$_6$H$_4$—CF$_3$ |
| 3 | F | Cl | H | —CH$_2$—C(CH$_3$)=N—O—CH(CH$_3$)C$_2$H$_5$ |
| 4 | F | Cl | H | —C(CH$_3$)$_2$—C(CH$_3$)=N—O—C$_3$H$_7$—i |
| 5 | Br | H | H | —C$_3$H$_7$—i | in the presence of a base, at a temperature between 0° C. and 100° C.

28. A process according to claim 27 wherein the reaction is carried out in the presence of an ingredient selected from the group consisting of phase-transfer catalysts, diluents and mixtures thereof.

29. A compound according to claim 1, wherein the radicals A, B, Q, and R are as fined in Table 1 for Compound Nos. 2–5, 8, 16, 22, 35, 37, 39, 42–64, 66–76, 78–98, 100–101, 103–118, 120, 121–122 and 124.

30. A compound according to claim 1, wherein the radicals A, B, Q, and R are as defined in Table 1 for Compound Nos. 2, 5, 22, 37, 39, 45, 58, 61–62, 68–76, 78–98, 100–101, 103, 105–111, 116–118, 120, 121–122 and 124.

31. A compound according to claim 1, wherein the radicals A, B, Q, and R are as defined in Table 1 for Compound Nos. 37, 39, 45, 58, 61–62, 68, 91–92, 95—95, 100–101, 103, 105–106, 109–111, 116, and 125.

32. A compound according to claim 1, wherein a) A is other than H, F or Cl, or b) B is other than F or Cl.

33. A compound according to claim 1, wherein the radicals A, B, Q, and R are as defined in Table 1 for Compound Nos. 3–4, 8, 16, 35, 42–64, 66–67, 92, 103–106, and 109–117.

* * * * *